(12) United States Patent
Doerr et al.

(10) Patent No.: US 11,673,000 B2
(45) Date of Patent: Jun. 13, 2023

(54) DEVICE AND METHOD TO ACTIVATE CELL STRUCTURES BY MEANS OF ELECTROMAGNETIC ENERGY

(71) Applicant: BIOTRONIK SE & CO. KG, Berlin (DE)

(72) Inventors: Thomas Doerr, Berlin (DE); Ingo Weiss, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 523 days.

(21) Appl. No.: 16/451,299

(22) Filed: Jun. 25, 2019

(65) Prior Publication Data
US 2019/0388685 A1    Dec. 26, 2019

(30) Foreign Application Priority Data

Jun. 25, 2018   (DE) .................... 10 2018 115 180.2
Oct. 23, 2018   (EP) .................................... 18202080

(51) Int. Cl.
*A61N 5/06*    (2006.01)
*A61N 1/05*    (2006.01)
(Continued)

(52) U.S. Cl.
CPC .......... *A61N 5/0601* (2013.01); *A61B 5/0071* (2013.01); *A61B 5/4094* (2013.01); *A61B 5/686* (2013.01); *A61B 5/7221* (2013.01); *A61B 5/7228* (2013.01); *A61B 5/7253* (2013.01); *A61B 5/7264* (2013.01); *A61B 5/7282* (2013.01); *A61N 1/059* (2013.01); *A61N 1/0534* (2013.01); *A61N 1/0551* (2013.01); *A61N 1/0558* (2013.01); *A61N 1/0587* (2013.01); *A61N 1/0595* (2013.01); *A61N 1/06* (2013.01); *A61N 1/08* (2013.01); *A61N 1/3621* (2013.01);
(Continued)

(58) Field of Classification Search
CPC . A61N 5/06; A61N 1/372; A61N 1/05; A61N 1/362; A61N 5/10; A61K 48/00; A61B 5/00; A61B 5/046; A61B 5/0464
See application file for complete search history.

(56) References Cited

U.S. PATENT DOCUMENTS 9,622,809 B2    4/2017  Weinberg
2009/0088680 A1  4/2009  Aravanis et al.
(Continued)

FOREIGN PATENT DOCUMENTS

WO    2014126927 A1    8/2014

OTHER PUBLICATIONS

Wang, et al., "Optogenetic control of heart rhythm by selective stimulation of cardiomyocytes derived from pnmt+ cells in murine heart", Scientific Reports, Jan. 13, 2017, pp. 1-10, URL: https://ora.ox.ac.uk/objects/uuid:39b36814-ec0d-4091-9fd6-e4241c9c1a9a.
(Continued)

*Primary Examiner* — Michael W Kahelin
(74) *Attorney, Agent, or Firm* — Laurence A. Greenberg; Werner H. Stemer; Ralph E. Locher

(57) ABSTRACT

An implantable device for implantation in a human body or animal body. The device includes an energy source, an energy storage device, and an electronics unit. Further, an actuator is coupled with the energy storage device and it is configured to emit electromagnetic waves by discharging the energy storage device.

13 Claims, 35 Drawing Sheets

(51) Int. Cl.
| | |
|---|---|
| A61N 1/06 | (2006.01) |
| A61N 1/362 | (2006.01) |
| A61N 1/37 | (2006.01) |
| A61N 1/372 | (2006.01) |
| A61N 1/36 | (2006.01) |
| A61N 1/378 | (2006.01) |
| A61B 5/00 | (2006.01) |
| A61N 2/00 | (2006.01) |
| A61N 1/08 | (2006.01) |
| A61N 5/073 | (2006.01) |
| A61B 5/01 | (2006.01) |
| A61B 5/05 | (2021.01) |
| A61B 5/1455 | (2006.01) |
| A61B 7/04 | (2006.01) |
| A61B 8/00 | (2006.01) |
| A61N 5/10 | (2006.01) |
| A61B 5/363 | (2021.01) |
| A61N 5/067 | (2006.01) |

(52) U.S. Cl.
CPC ....... *A61N 1/3629* (2017.08); *A61N 1/36064* (2013.01); *A61N 1/36067* (2013.01); *A61N 1/36071* (2013.01); *A61N 1/36153* (2013.01); *A61N 1/371* (2013.01); *A61N 1/378* (2013.01); *A61N 1/37223* (2013.01); *A61N 1/37235* (2013.01); *A61N 2/002* (2013.01); *A61N 5/06* (2013.01); *A61B 5/01* (2013.01); *A61B 5/05* (2013.01); *A61B 5/14551* (2013.01); *A61B 5/363* (2021.01); *A61B 5/4082* (2013.01); *A61B 5/4836* (2013.01); *A61B 7/04* (2013.01); *A61B 8/00* (2013.01); *A61B 2562/0204* (2013.01); *A61B 2562/0219* (2013.01); *A61B 2562/0223* (2013.01); *A61B 2562/0247* (2013.01); *A61B 2562/0271* (2013.01); *A61N 1/36082* (2013.01); *A61N 5/067* (2021.08); *A61N 5/10* (2013.01); *A61N 2005/063* (2013.01); *A61N 2005/0612* (2013.01); *A61N 2005/0626* (2013.01); *A61N 2005/0628* (2013.01); *A61N 2005/0632* (2013.01); *A61N 2005/0633* (2013.01); *A61N 2005/0643* (2013.01); *A61N 2005/0658* (2013.01); *A61N 2005/0659* (2013.01); *A61N 2005/0661* (2013.01); *A61N 2005/0662* (2013.01); *A61N 2005/0666* (2013.01); *A61N 2005/0667* (2013.01); *A61N 2005/0668* (2013.01); *A61N 2005/073* (2013.01)

(56) References Cited

U.S. PATENT DOCUMENTS

| | | |
|---|---|---|
| 2012/0290025 A1 | 11/2012 | Keimel |
| 2013/0238048 A1* | 9/2013 | Almendinger .......... H02J 7/007 607/40 |
| 2016/0066789 A1* | 3/2016 | Rogers .................... A61N 1/05 604/20 |
| 2018/0140862 A1 | 5/2018 | Stahler et al. |
| 2018/0256906 A1* | 9/2018 | Pivonka ................. A61N 1/378 |

OTHER PUBLICATIONS

Lung et al.: "Activation of the Mammalian Cells by Using Light-Sensitive Ion Channels", Methods in Molecular Biology, vol. 875, Chapter 12, DOI 10.1007/978-1-61779-806-1_12, Springer Science+Business Media New York, 2012, pp. 241-251.

* cited by examiner

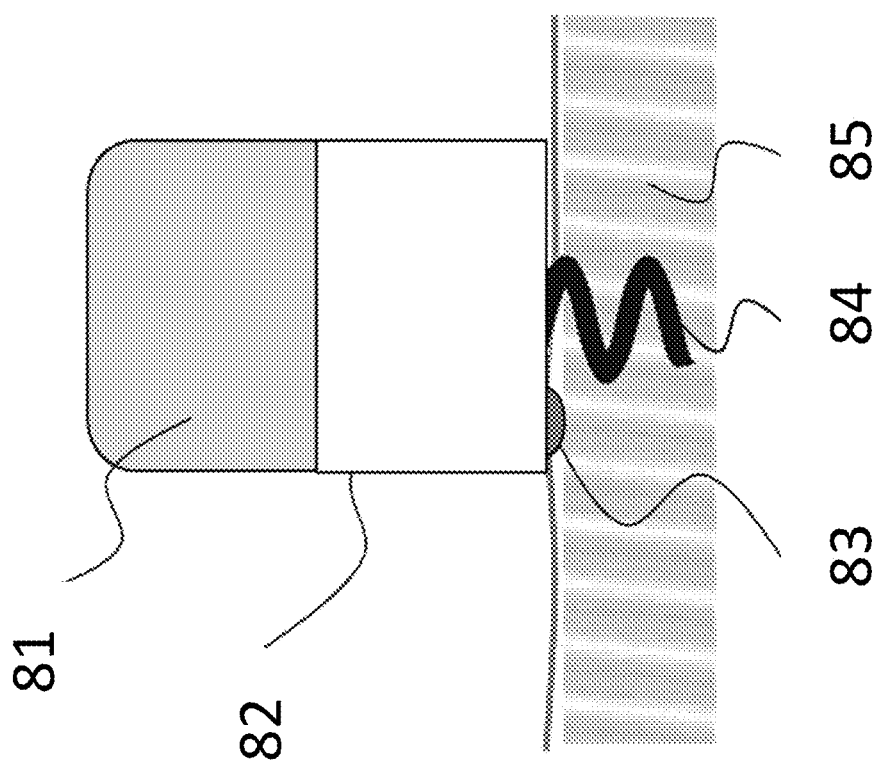

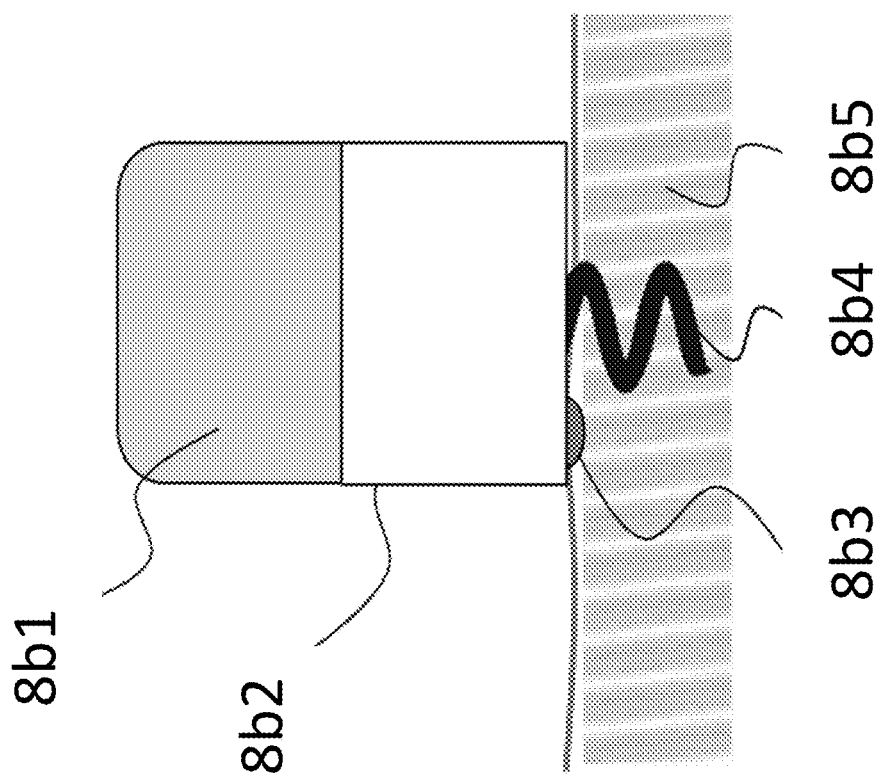

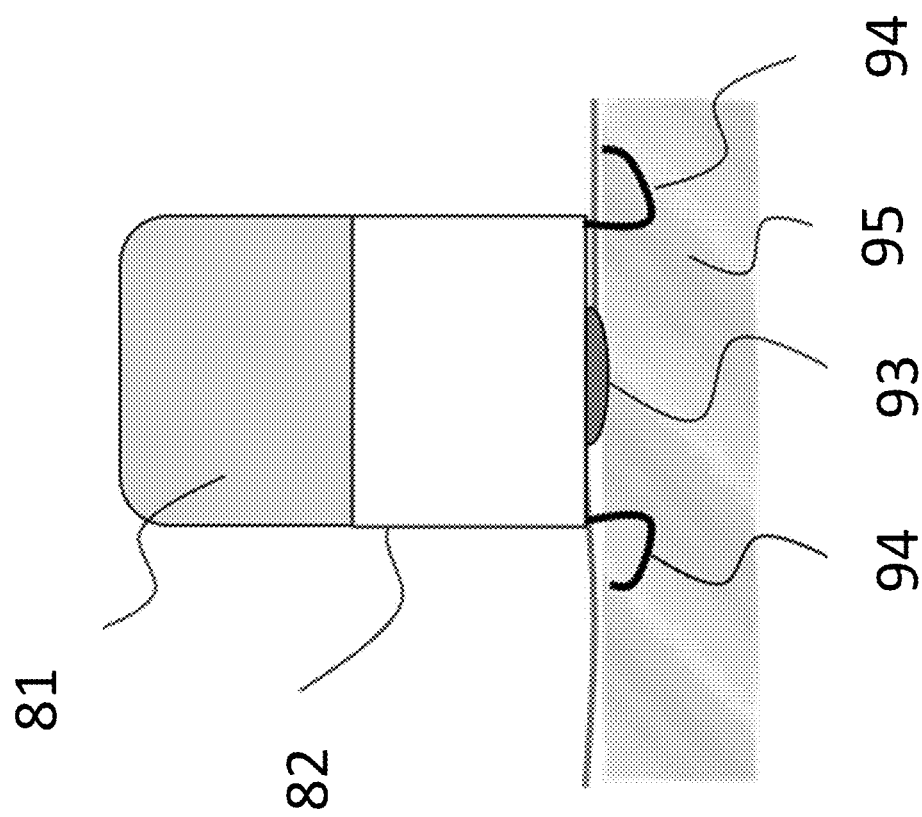

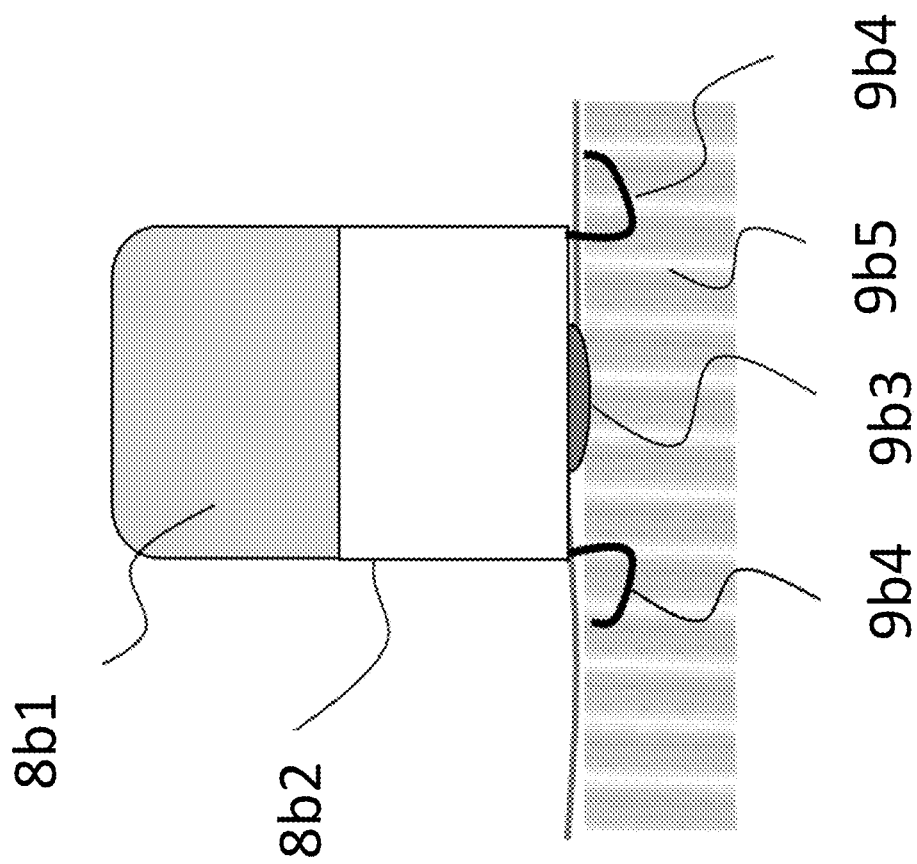

|  | RV | CAN | RA |
|---|---|---|---|
| Electromagnetic Actuator | X |  |  |
| Shock Vector |  | X | X |
| Electromagnetic Actuator | X | X |  |
| Shock Vector | X |  | X |
| Electromagnetic Actuator | X |  | X |
| Shock Vector |  | X | X |
| Shock Vector | X | X |  |
| Electromagnetic Actuator |  | X | X |
| Shock Vector | X | X |  |
| Electromagnetic Actuator | X |  | X |
| Shock Vector | X |  | X |
| Electromagnetic Actuator |  | X | X |

FIG. 23

DEVICE AND METHOD TO ACTIVATE CELL STRUCTURES BY MEANS OF ELECTROMAGNETIC ENERGY

CROSS-REFERENCE TO RELATED APPLICATION

This application claims the priority, under 35 U.S.C. § 119, of German patent application DE 10 2018 115 180.2, filed Jun. 25, 2018, and European patent application No. EP 18202080.0, filed Oct. 23, 2018; the prior applications are herewith incorporated by reference in its entirety.

BACKGROUND OF THE INVENTION

Field of the Invention

The invention describes a device and method to activate cell structures by way of electromagnetic energy.

Stimulators to stimulate human or animal tissue by electric current have been known for a long time. Electric stimulation of nerve tissue causes the activation of action potentials, which are used in medical therapy and diagnosis. Examples of implantable stimulators are, among others, implantable cardiac pacemakers and defibrillators, spinal cord stimulators, vagus nerve stimulators, and brain pacemakers.

Electrical stimulation devices are galvanically coupled to human or animal tissue and measure electrical potentials and/or stimulate the tissue by delivering electric current to trigger action potentials. Disadvantages of electrical stimulation result because of the necessary galvanic connection to the tissue, among other things. The direct contact of stimulation electrodes with the tissue and coupling of current can cause, e.g., necroses, electrical after-potentials, which limit sensing functions, crosstalk (i.e., interference in the case of parallel stimulation over different stimulation pathways), unwanted external induction of therapeutic currents (e.g., produced by the high-frequency magnetic fields inside an MRI machine), possible pain events, electroporation, or unwanted stimulation of nearby tissue (e.g., heart stimulators can cause unwanted costimulation of the phrenic nerve). Other disadvantages result from therapeutic current generation devices, which can be elaborate and voluminous (e.g., the charging circuit in an implantable cardioverter-defibrillator) and limitations on the accessibility of the target tissue.

For some years, the genetic manipulation of tissue to generate excitability by means of electromagnetic waves has been the subject of scientific discussion and research. Target tissue has been successfully genetically modified so that action potentials can be evoked by electromagnetic waves.

One of these methods is referred to as optogenetic manipulation. This method is described, for example, in Lung M S, Pilowsky P, Goldys E M., "Activation of the Mammalian cells by using light-sensitive ion channels." Methods Mol Biol. 2012; 875:241-51; this publication describes optogenetic manipulation of tissue to trigger action potentials by means of light in the visible spectrum;

Wang et al. "Optogenetic Control of Heart Rhythm by Selective Stimulation of Cardiomyocytes Derived from Pnmt+ Cells in Murine Heart", January 2017 in Scientific Reports.

United States patent application publication US 2009/0088680 A1 describes a catheter-based system to introduce an optical fiber into the heart, the cardiac tissue having previously been treated by means of optogenetic manipulation. In order to convey the optical fiber into the interior of the heart, a vascular access is placed in the patient, a catheter is pushed forward into the heart, and the optical fiber is delivered to the interior of the heart through the catheter. The optical fiber carries light into the heart and performs endocardial stimulation of the manipulated tissue.

A disadvantage of the method described in US 2009/0088680 A1 is that it must be performed on an outpatient basis by a doctor, and the optical fiber must be operated from an external device. There are also disadvantages caused by the venous vascular access and the catheterization, such as, for example, infections and vascular occlusions.

SUMMARY OF THE INVENTION

The goal of the invention is to evoke, modulate, terminate, and/or inhibit action potentials on pretreated excitable cell structures of animals and/or humans, and to do so in a permanently implantable device without this requiring the impression of galvanic electric current.

The goal is also to allow stimulation therapy of manipulated tissue with electromagnetic radiation by means of common implantable pulse generators (IPGs).

One goal of this invention is to provide a device and a system that does not have the mentioned disadvantages.

Another goal of this invention is to provide a device and a system for stimulation of tissue by means of electromagnetic waves to trigger action potentials, the device allowing a permanent stimulation, without this requiring a permanent vascular access, external equipment, or an outpatient visit to the doctor.

With the above and other objects in view there is provided, in accordance with the invention, an implantable device, comprising:

an energy source, an energy storage device, and an electronics unit;

an actuator connected to the energy storage device and configured to emit electromagnetic waves by discharging the energy storage device;

the electronics unit including a controller, the controller having at least one of the following properties:

the controller controls a charging of the energy storage device and a discharging of the energy storage device to the actuator;

the controller controls an amount of energy for charging and discharging;

the controller is externally configurable by way of a programming device;

the controller has a release unit for discharging;

the controller adjusts at least two impedances that are connected in series and the discharging takes place over the at least two series-connected impedances;

the controller controls the discharging so that the actuator emits electromagnetic waves during a time period from 0.1 ms to 5 s.

According to one exemplary embodiment of the invention, the actuator is designed to emit electromagnetic waves for stimulation of optogenetically manipulated tissue.

An implantable device for stimulation of genetically manipulated tissue solves the previously addressed problems. An implant can provide permanent stimulation, without requiring catheterization of the patient or an operation by the doctor.

Preferably, the stimulation by the inventive stimulation device is designed to treat at least one of the following diseases:
cardiac bradycardia;
cardiac tachycardia;
atrial fibrillation;
ventricular fibrillation;
heart failure;
Parkinson's disease;
tremor;
dystonia;
depression;
Tourette's syndrome;
chronic pain;
epilepsy;
neuronal or muscular disorders.

According to one exemplary embodiment of the inventive stimulation device, the actuator is designed to emit electromagnetic waves in the frequency spectrum from infrared light to X-ray radiation. According to a preferred embodiment, the actuator is designed to emit electromagnetic waves in the frequency spectrum between $10^{13}$ and $10^{20}$ Hz. Preferably, the actuator is designed to emit electromagnetic waves in the frequency spectrum between $10^{13}$ and $10^{16}$ Hz, which corresponds to the spectrum from infrared radiation to ultraviolet radiation, inclusive. According to one exemplary embodiment the actuator is designed to emit electromagnetic waves in the frequency spectrum between $10^{14}$ and $10^{15}$ Hz, which approximately corresponds to the spectrum that is visible for the human eye. An advantage of this choice is the relatively simple implementation of such an actuator, and small energy demand and the harmlessness of light to human or animal tissue. In the framework of this invention, the indicated limits of the frequency range should not be interpreted as hard limits, but rather should lie approximately at the indicated frequency within a certain tolerance. The tolerance should be based on the understanding of the person skilled in the art. In particular, the tolerance should be based on what frequencies in the electromagnetic spectrum the person skilled in the art associates with a corresponding radiation type (e.g., the spectrum of visible light, X-ray radiation, infrared radiation).

In a preferred embodiment of the invention, the stimulation device comprises at least one housing, which in turn comprises a biocompatible material. Preferably, that part of the stimulation device that comes in direct contact with human or animal tissue when the stimulation device is in the implanted state consists of a biocompatible material, so that the organism does not recognize the stimulation device as a foreign body, thus preventing a biological defense reaction.

According to one embodiment of this invention, the housing is hermetically sealed, so that in the implanted state no body fluids can penetrate into the interior of the housing.

According to another aspect of the inventive stimulation device, the electronics unit is arranged within the housing, the energy source and/or the actuator being arranged inside the housing or outside the housing. Arranging components inside a housing presents the advantage that the compactness of the device is increased and wiring pathways are minimized. In addition, all components inside the housing are protected from external influences. Arranging the actuator outside the housing presents the advantage that this allows greater flexibility in the placement of the actuator. This allows the actuator to be placed so that the area to be stimulated is irradiated with electromagnetic waves in a locally more targeted manner. If a rechargeable battery and a housing made of electrically conductive material are used, arranging the battery outside the housing presents the advantage that a recharging process (e.g., inductively by an external coil) is more efficient than if the battery is arranged within the housing, since eddy current losses due to the housing material are reduced.

Furthermore, one embodiment of the inventive provides that the electronics unit have at least one of the following or a combination of the following units:
a pickup unit designed to measure data that characterizes the tissue activity and/or success of a stimulation; and/or
an evaluation unit to evaluate measurement data with respect to the requirement of a stimulation and/or with respect to the success of a stimulation.

For example, the controller can be designed to vary one of the following properties or a combination of the following properties of the electromagnetic waves used for the stimulation:
the intensity, i.e., the amplitude of the electromagnetic waves;
the frequency;
the duration of a wave train; and/or
the pulse duty ratio of the electromagnetic waves, i.e., the ratio between the duration of emission of electromagnetic waves and the time delay between them, in order to modulate the electromagnetic wave or the electromagnetic signal.

According to one aspect of this invention, the duration of a wave train is 0.1 ms to 5 s, depending on the intended effect of the stimulation by the electromagnetic waves. A wave train is understood to mean a continuous electromagnetic wave. For example, it is possible to select a wave train with a duration of 0.1 ms to 2 ms for an application in neurostimulation, as a pacemaker stimulus for stimulation of the heart, or as the duration of one stimulus in a sequence of antitachycardia pacing stimuli (ATP). A duration of 0.1 s to 5 s can be selected, e.g., as a cardioversion or defibrillation stimulus for the stimulation of the heart.

Furthermore, according to one exemplary embodiment of this invention, the frequency of stimulation by means of electromagnetic waves lies in the frequency spectrum between $10^{13}$ and $10^{20}$ Hz. According to a preferred exemplary embodiment, a frequency in the range: $10^{13}$-$10^{16}$ or $10^{14}$-$10^{15}$ Hz is selected.

According to another aspect of the inventive stimulation device, the stimulation device has at least one electrode lead or electrode probe. For example, the stimulation device can have a long stretched-out, flexible electrode lead, such as are used for common cardiac pacemakers or neurostimulators. According to one embodiment, the actuator can be arranged at the distal end such an electrode lead.

For example, according to one embodiment, the pickup unit can be designed to receive electromagnetic waves and to convert them into electrically storable measurement data. Such a pickup unit can comprise a light sensor, such as, for example, a photodetector. The information about the electromagnetic waves that is picked up is converted into measurement data and can then be analyzed by means of the evaluation unit. The evaluation unit can evaluate the measurement data, for example, with respect to various parameters which represent a physiological state of the patient and/or a state of the stimulation device itself. Examples of such parameters are: success of a stimulation therapy, state of need for a stimulation therapy, a health state of the patient, a parameter characterizing the state of the environment of the stimulation device, etc.

Furthermore, according to a preferred embodiment of this invention, at least the energy source and the electronics unit are arranged inside the housing. These units are sensitive to the body fluids, some of which are aggressive, to which they would be exposed in the implanted state. Therefore, according to one embodiment, placement in a hermetically sealed housing is advantageous.

In a preferred embodiment, the electronics unit is at least partly configurable by an external device. The configuration can be wireless or wired, by coupling an external device to the electronics unit. This allows the functions of the inventive stimulation device to be flexibly programmed and adapted to an individual patient.

According to another aspect of this invention, the stimulation device comprises at least one fixing unit, which is designed to fix at least one part of the stimulation device into the tissue of a human or animal body. Examples of such a fixing unit are: screw elements, hook elements, anchor elements, and tissue adhesive.

According to one exemplary embodiment of this invention, the energy source comprises a battery in the form of a primary cell or a secondary cell. The battery is preferably arranged inside the housing. According to one exemplary embodiment, the battery is rechargeable, e.g., inductively through an external charger with a charging coil.

Furthermore, according to a preferred embodiment of this invention, the stimulation device has a telemetry unit for wireless communication with at least one external device and/or data center. This allows the stimulation device to send measurement data and receive other data, such as, for example programming commands, patient-specific data, etc.

According to one embodiment of this invention, the actuator comprises at least one optical fiber. The optical fiber serves for coupling the electromagnetic waves for stimulation of optogenetic tissue.

Furthermore, according to other embodiments of this invention, the stimulation device can comprise one of the following sensors or a combination of the following sensors:
 an accelerometer;
 a temperature sensor;
 an acoustic sensor;
 an ultrasound sensor;
 an oxygen sensor;
 a pressure sensor; and/or
 a magnetic field sensor.

According to one embodiment of this invention, additional sensors can be coupled with the evaluation unit. The evaluation unit can evaluate the sensor data, for example, with respect to various parameters which represent a physiological state of the patient and/or a state of the stimulation device itself. Examples of parameters are: success of a stimulation therapy, state of need for a stimulation therapy, a health state of the patient, a parameter characterizing the state of the environment of the stimulation device, etc.

According to another aspect of this invention, the stimulation device is designed to output a stimulation by electromagnetic waves to the cardiac tissue. This stimulation is performed at a certain time relative to a heartbeat. For example, in a signal representing the heartbeat it is possible to measure a characteristic event (e.g., an episode of bradycardia/tachycardia, an abnormality in the signal shape, etc.), following which a counter is started. If the counter finds that a time interval has passed, the stimulation is carried out. The stimulation is designed to cause at least one contraction of the heart.

According to one embodiment of the invention, this stimulation is output in the form of at least one stimulus,
 if the evaluation unit detects a requirement for therapy of bradycardia, the detection being based on the measured heart rate falling below at least one specified heart rate; and/or
 if the evaluation unit detects a requirement for therapy of ventricular fibrillation, the detection being based on the comparison of at least one specified ventricular frequency and/or a specified stability of a ventricular frequency with a measured ventricular frequency.

In this embodiment, the stimulation device is designed for therapy of bradycardia or ventricular fibrillation.

According to one aspect of the invention, this stimulation is output in the form of multiple stimuli if the evaluation unit detects a requirement for therapy of tachycardia, the detection being based on the measured heart rate falling below at least one specified heart rate, multiple stimuli being output in a sequence; and/or If the evaluation unit detects a requirement for cardiac resynchronization therapy, the detection being based on the evaluation of measurement data which represents the cardiac activity, at least one first and one second stimulus being output and the at least first and second stimulus being designed to produce an essentially synchronous contraction of a left and a right half of the heart.

According to one aspect of the invention, this stimulation is output in the form of multiple stimuli if the evaluation unit detects a requirement for therapy of tachycardia, the detection being based on the measured heart rate exceeding at least one specified heart rate, and the stimuli being output in a sequence and being designed to terminate the tachycardia. The tachycardia is atrial and/or ventricular tachycardia or atrial fibrillation. The detection of atrial fibrillation is based, for example, on comparison of at least one specified atrial frequency and/or a specified stability of an atrial frequency with the measured atrial frequency. According to one exemplary embodiment, the stimuli of the sequence are designed to terminate the atrial fibrillation.

In the two previously mentioned embodiments, the stimulation device is designed for therapy of a tachycardia or therapy of a heart failure caused by asynchronous contraction of the right and left halves of the heart.

According to one aspect of the invention, this stimulation is output in the form of at least one stimulus, if the evaluation unit detects a requirement for therapy of ventricular fibrillation. The detection of the requirement for therapy is based on comparison of at least one specified ventricular frequency and/or a specified stability of a ventricular frequency with the measured ventricular frequency. The at least one output stimulus is designed to terminate the ventricular fibrillation.

According to one aspect of this invention, the stimulation device further comprises one or more pickup units in one or more heart chambers. For example, pickup units can be arranged in the right atrium or the right ventricle. The pickup units are preferably arranged so that they can receive signals from the right atrium, right ventricle, left atrium, and/or left ventricle. The signals can be, for example, of an electromagnetic, electrical, or acoustic nature.

According to another exemplary embodiment of this invention, the stimulation device outputs the stimulus or stimuli after the passage of a time interval relative to a heartbeat. This controller has a timer or counter that can start or end the time interval. The starting and ending of the time interval is triggered by the pickup unit, a stimulation being triggered after the time interval has passed.

The invention proposes a process for controlling an implantable stimulation device, this process comprising at least the steps:
 Inducing the stimulation device to emit electromagnetic waves, triggering a stimulation of genetically manipulated tissue by said electromagnetic waves.

The previously mentioned aspects and embodiments of the inventive stimulation device and the components it comprises are to be applied in the same way to the process to control the same and to control the components that the inventive stimulation device comprises.

Furthermore, another aspect of the inventive stimulation device, it comprises an implantable stimulator without a long stretched-out electrode lead. The electrode or probe lines that are frequently used in connection with electrical stimulation can present an additional source of complications for infections or line breaks or short circuits.

According to one aspect of the invention; the stimulation device comprises at least:
an energy source;
an electronics unit that comprises a controller;
an actuator that is coupled with the electronics and/or the energy source;
a housing, wherein the energy source, the electronics unit and the actuator are arranged;
a fixing unit which is coupled with the housing and which is designed to fix the stimulation device on a heart or in a heart. The actuator is designed to emit electromagnetic waves for stimulation of genetically manipulated tissue. The controller is designed to control the stimulation of the tissue by means of the electromagnetic waves of the actuator.

Furthermore, according to one exemplary embodiment of this invention, the electronics unit has at least one of the following or a combination of the following units:
a pickup unit designed to measure data that characterizes the tissue activity and/or success of a stimulation; and/or
an evaluation unit to evaluate measurement data with respect to the requirement of a stimulation and/or with respect to the success of a stimulation.

According to one embodiment of this invention, at least part of the actuator is coated with a biocompatible material. In particular, if the actuator is arranged outside of the housing and is in direct contact with its environment, i.e., in the implanted state in contact with body fluids, the actuator requires such a biocompatible coating. According to one aspect of the inventive stimulation device, the actuator is designed to stimulate a local area on or in the heart by means of electromagnetic waves.

According to one exemplary embodiment of this invention, the stimulation device preferably has at least one first and one second actuator that are designed to stimulate different local areas on or in the heart by means of electromagnetic waves.

A second actuator can be connected with the electronics unit and/or controller of the stimulation device and can be controlled by the same.

According to one exemplary embodiment, the fixing unit and/or at least parts of the housing is/are provided with an anti-inflammatory medication, e.g., a steroid.

It would also be conceivable for the inventive stimulation device to have a unit for electrical stimulation of the heart. The stimulation device could be controlled so that it triggers a stimulation of the tissue by means of electromagnetic waves or by means of galvanically coupled currents, or by a combination of the two. Electromagnetic waves would be transmitted by the actuator, while galvanic currents are coupled by the unit for electrical stimulation of the heart.

According to one aspect of this invention, the stimulation device comprises:
an energy source;
an electronics unit that comprises a controller;
an actuator that is coupled with the electronics and/or the energy source, this actuator being designed to emit electromagnetic waves for stimulation of genetically manipulated tissue;
a fixing unit;
the stimulation device being designed for at least temporary implantation in the human or animal body, and the controller being designed to control the stimulation of said tissue by means of the electromagnetic waves of the actuator. To accomplish this, the stimulation device has a control unit that receives data that picks up the tissue activity and/or the success of a stimulation by a stimulation carried out through the electromagnetic actuator.

Furthermore, according to other exemplary embodiments of this invention, the control unit receives said data on the basis of at least one or a combination as the following signals:
an electrically derived far field signal;
heart sounds;
a pressure signal;
an optical signal according to the principle of pulse oximetry;
an ultrasound signal;
an acceleration signal; and/or
a thermal signal.

According to one exemplary embodiment, the stimulation device is designed to receive and to evaluate an ultrasound signal on the basis of Doppler technique, in order to be able to draw conclusions in this way about the flow rates and directions of body fluids.

According to one exemplary embodiment of the inventive stimulation device, the control unit is not in electrical contact with the genetically manipulated tissue. The control unit is arranged in such a way that the signals to be evaluated, which characterize the tissue activity and/or success of a stimulation by means of the actuator, can be received, by sensors, directly from the control unit. Alternatively, the sensors can be arranged so that they are separated from the control unit. In this case, the signals received by the sensors are forwarded to the control unit. The control unit can form a part of the electronics unit.

One exemplary embodiment of this invention describes a stimulation system that comprises at least:
an energy source;
an electronics unit that comprises a controller;
an actuator that is coupled with the electronics and/or the energy source, this actuator being designed to emit electromagnetic waves for stimulation for genetically manipulated tissue;
a housing in which at least the electronics unit is arranged;
the stimulation system being designed for at least temporary implantation in the human or animal body, and the controller being designed to control the stimulation of said tissue by means of the electromagnetic waves of the actuator. The stimulation system also comprises a selector that is designed to select the region or area of the said tissue for the stimulation.

According to one aspect of the inventive stimulation system, the actuator is designed to emit the electromagnetic waves in at least one emission direction, and the selector is designed to control the emission direction.

According to one exemplary embodiment, the actuator emits electromagnetic waves in a solid angle of less than $4*\pi$.

According to one exemplary embodiment of the inventive stimulation system, the selector further has at least one masking device or mask designed to mask an area of said tissue, so that the intensity of the stimulation for the area is reduced or equal to zero.

According to one exemplary embodiment, the masking device is designed to change a solid angle with which the actuator emits the electromagnetic waves.

According to one exemplary embodiment, the masking device comprises at least one filter that blocks
  electromagnetic radiation of certain frequency ranges; or
  electromagnetic radiation of certain polarization directions.

According to one exemplary embodiment, the masking device is connected with the actuator or fixed to the actuator. Alternatively, it can form a unit with the actuator.

According to one exemplary embodiment, the masking device is in contact with the area of said tissue. A specific exemplary embodiment would involve the masking device being in the form of a covering layer (e.g., a color that is impervious to electromagnetic radiation) or covering device that covers said tissue areas. Furthermore, according to one exemplary embodiment of this invention, the masking device is formed by part of the housing. This can be realized, for example, by putting the masking device on the housing (e.g., in the form of shades).

Furthermore, according to one exemplary embodiment, the actuator is arranged in such a way that when the stimulation system is in the implanted state, an object in the environment serves to mask at least one area of said tissue, so that the intensity of the stimulation for the area is reduced or equal to zero. For example, this can be accomplished by arranging the actuator in a cavity in the environment of the implantation site, so that the tissue topology surrounding it serves as a natural mask for the emitted electromagnetic waves. If the stimulation system is implanted in the heart, then the actuator can be implanted in the atrial appendage, which is located in the right atrium. This precludes the possibility of electromagnetic waves being irradiated into the right ventricle, i.e., allows selective irradiation for the atrium. In another example, if the actuator is implanted below the moderator band, then no electromagnetic waves can be irradiated into the atrium, i.e., selective irradiation into the right ventricle becomes possible.

According to another aspect of the inventive stimulation system, the said tissue irradiation area is changeable by adapting the masking device. For example, based on measurements of the success of the stimulation, it can be necessary to improve the treatment of the cell structures. This can possibly involve expanding the area for the irradiation by additional treatment or reducing it using the masking device.

According to one embodiment of the inventive stimulation system, the selector has a support structure, which is connected with the housing, the actuator being connected with the support structure. The support structure can be designed so that the selector and/or the actuator can be arranged and fixed at different places on the support structure. This makes it possible to change the spatial arrangement between selector and actuator and thus more flexibly adapt the emission angle of the actuator. According to one exemplary embodiment, the support structure is designed to limit the emission angle of the electromagnetic waves that are emitted by the actuator.

Furthermore, according to one aspect of the inventive stimulation system, the stimulation system has at least one first and one second actuator. The actuators are preferably arranged so that interference is minimized if they emit electromagnetic waves simultaneously. For instance, two tissue areas can be irradiated independently of one another. According to one aspect of the invention, the electromagnetic waves emitted by the first and second actuators have different frequencies and/or different polarization.

Furthermore, according to one exemplary embodiment of the inventive stimulation system, the stimulation system has means of focusing electromagnetic radiation. Means for focusing comprise, for example:
  lenses;
  collimators;
  devices that possess materials with anisotropic propagation characteristics for the electromagnetic radiation that is being used.

An example of the invention is explained in detail below using a exemplary embodiment that is illustrated in drawings. In the figures, all elements that are functionally the same or have the same effect are labeled with the same reference numbers. The Figure is a schematic representation of the invention and depicts non-specific parameters of the invention. The figure only reproduces typical embodiments of the invention, and is not intended to limit the invention to the embodiments shown.

According to the invention, there is proposed a device that comprises:
  an energy source;
  energy storage;
  an electronics unit;
  the device being designed for implantation in the human or animal body;
  and an actuator that is coupled with the energy storage and that is designed to emit electromagnetic waves by discharging the energy storage.

Furthermore, according to one aspect of this inventive device, the energy storage has a capacitor and/or a coil.

According to one aspect of this inventive device, the electronics unit comprises a controller, which has at least one of the following properties:
  it is designed to control the charging of the energy storage and discharging of the energy storage to the actuator;
  it is designed to control the amount of energy for charging and discharging;
  it is externally configurable by means of a programming device;
  it has a release unit for discharging; and/or
  the discharging takes place over at least two impedances that are connected in series, the impedances being adjustable by means of the controller.

For example, such impedances can be realized by electrical switch elements. Thus, such switch elements allow the discharge to proceed.

According to one exemplary embodiment of the inventive device, the discharge is controlled by the controller so that the actuator emits electromagnetic waves in the form of a continuous wave train in a period of time from 0.1 ms to 5 s. For a neurostimulation application (e.g., spinal cord stimulation, vagus nerve stimulation), cardiac pacing, or ATP stimulation, it is possible to select a period of time from 0.1 ms to 2 ms; for cardioversion or defibrillation of the heart, it is possible to select 0.1 s to 5 s.

Furthermore, according to one aspect of the invention, the discharge takes place in more than one phase.

According to one exemplary embodiment of the inventive device, the actuator has at least one of the following properties:
  it comprises at least one light source for emission of the electromagnetic waves;

it comprises at least one current limiter (e.g., a resistor or a diode);

it is operated by the energy storage with 1 V to 1,500 V (special solutions would be, e.g.: 1-10 V for a parallel circuit, 50-500 V for a series circuit) and/or it is arranged separately from a housing of the device and has a plug-and-socket connector, which is compatible with a plug socket of an implantable device for electrical cardiac stimulation.

According to another aspect of the invention, the light source comprises a series circuit of LEDs (light emitting diodes), a parallel circuit of LEDs, or a combination of a series circuit and a parallel circuit of LEDs. The use of LEDs offers, among other things, the advantages that the miniaturization of the light source is made possible in a simple way and the energy consumption is kept small, which can be decisive factors, especially for implementation in an implant.

According to another aspect of the invention, the light source comprises a laser light source, which has laser light of a wavelength that is suitable for the stimulation of genetically manipulated tissue. Laser light allows stimulation with very high local precision.

According to one exemplary embodiment of this invention, an implantable stimulation device is proposed for stimulation of cardiac tissue or nerve tissue structures, this implantable stimulation device having said inventive device. The device can have at least one stimulation electrode.

According to one aspect of the inventive stimulation device, it is designed to cause stimulation of cardiac tissue, the stimulation taking place
  by means of the actuator by electromagnetic waves; or
  by means of electrical stimulation;
  the stimulation by electromagnetic waves and by electrical stimulation taking place individually, consecutively, or simultaneously;
  the stimulation taking place in one area or multiple areas of the tissue.

According to one aspect of this invention; the stimulation device further comprises:
  a plug contact that is compatible with an actuator; and/or
  a plug contact that is compatible with an electrode for electrical stimulation; and/or
  an actuator and an electrode.

According to one exemplary embodiment of the stimulation device, it outputs, through the actuator, electromagnetic waves for stimulation of said manipulated tissue, it has success control, and, if the electrical therapy is unsuccessful, it outputs additional therapy. For example, it is also possible to output both types of therapy simultaneously, or to switch over between the two selectively. At what places what form of therapy is used can be programmable, or/and this is determined and switched, if necessary, by the stimulation device itself by analyzing the past success of the therapy. Preferably, the inventive stimulation device has dedicated connections for the electromagnetic actuator.

In a preferred embodiment, the inventive stimulation device has at least one connection that can be used both for an inventive actuator and also for prior art electrical stimulation. According to one embodiment, the actuator is connectable with the stimulation device through a plug that corresponds to a plug for a comparable component for electrical therapy (e.g., a plug of an electrode lead for cardiac stimulation). Preferably, the inventive actuator is operated by the same or at least similar voltages as those that are used for the prior art electrical therapy (e.g., cardiac pacemaker therapy, neurostimulators).

One exemplary embodiment of the invention proposes a device that is implantable in the human or animal body and that comprises at least one substance. The substance is designed to modify human or animal cell structures so that action potentials in the cell structures can be detected and/or evoked by irradiation with electromagnetic waves in the frequency range $10^{13}$-$10^{20}$ Hz. In this case, the device comprises application means to deliver the substance to the tissue.

Furthermore, according to one aspect of this invention, the application means to deliver the substance to the tissue comprise at least one of the following means:
  a cannula;
  means to spray, brush, dribble, and/or stamp the substance on.

According to one exemplary embodiment of this invention, the device has at least one supply line for the substance. It should also be considered that the device have at least one preservation device for the substance.

According to one exemplary embodiment, the device has a reservoir that is designed to store the substance. The device can have a housing, the reservoir being arranged inside the housing or outside of the housing. The reservoir can have a biocompatible envelope, and/or thermal insulation, and/or a protection against hard radiation. This allows the substance inside the reservoir to be protected effectively from external influences.

According to one aspect of the inventive device, the device has a port for filling the reservoir. The port can, e.g., be attached to the supply line, to the device housing, or to the reservoir. In one example, the port comprises a membrane. The membrane can have at least one of the following properties:
  it is positioned so that it is accessible by means of a tool for filling with the substance;
  it can be pierced multiple times; and/or
  it is designed so that it recloses after the tool for filling is removed, so that escape of the filled substance is essentially prevented.

According to one embodiment, the reservoir can form a part of the supply line.

Furthermore, according to one aspect of the inventive device, the preservation device has at least one of the following means:
  a thermal element for cooling and/or heating;
  a generator of radiation for sterilization;
  a storage for a preservative that can be added to the substance; and/or
  control means to determine a preservation status of the substance.

According to one exemplary embodiment, the inventive device comprises or is connectable with closed-loop control means. The closed-loop control means are designed to determine a degree of modification of the detectability and/or evocability of action potentials in the tissue by means of electromagnetic waves. The closed-loop control means can have at least one of the following properties:
  if it determines a low degree, it finds a need for the application means to deliver the substance, and/or
  the degree is determined on the basis of measurement data concerning the detection and/or evocation of action potentials in tissue by means of electromagnetic waves in the frequency range $10^{13}$-$10^{20}$ Hz.

According to one example, the inventive device comprises at least one of the following means:
  a valve to release the substance;
  a pump; and/or a masking device that is designed to mask tissue areas where no substance should be delivered.

Furthermore, according to one embodiment, the device comprises at least:
an energy source;
an electronics unit;
an actuator that is coupled with the electronics unit and/or the energy source, and that is designed to emit electromagnetic waves for stimulation of tissue treated by the substance.

According to one aspect, the delivery of the substance to the tissue by the application means is controllable over a period of time. For example, the application means can control the delivery of the substance over a period of time, e.g., by delivering predetermined doses at regular intervals. Alternatively, the application means can comprise means that are biodegradable over a longer period of time and that contain the substance. Contact with the tissue causes the biodegradable means together with the substance to be released output to the tissue in a time-controlled manner. In one example, the substance itself is degradable over a longer period of time.

According to one exemplary embodiment, a device is proposed that comprises at least:
an energy source;
an electronics unit;
a pickup unit that is coupled with the electronics unit and that is designed to measure electromagnetic waves in the frequency range $10^{13}$-$10^{20}$ Hz;
the device being designed for implantation in the human or animal body. The device is designed to detect that electromagnetic waves have been emitted from genetically manipulated tissue.

According to one aspect of the inventive device, this device has an actuator that is coupled with the electronics unit and/or the energy source and that is designed to emit electromagnetic waves in the frequency range $10^{13}$-$10^{20}$ Hz.

According to one aspect of the inventive device, the electronics unit is designed to recognize that electromagnetic waves measured by the pickup unit were emitted from the actuator. For example, they can be waves emitted by the actuator that are reflected off the tissue. The reflected waves are detected by the pickup unit and correspondingly recognized by the electronics unit.

For example, according to one aspect of the inventive device, the electromagnetic waves measured by the pickup unit are the electromagnetic waves emitted by the actuator in changed form. The change is based, e.g., on at least one of the effects:
reflection;
fluorescence;
absorption;
transmission; and/or
polarization.

In one example, the electronics unit is designed to recognize, in the electromagnetic waves measured by the pickup unit, at least one of the following parameters, a combination of them, or a variable derived from them:
amplitude;
frequency or frequency spectrum; and/or
polarization direction;
phase;
at least one of the following processes being used:
modulation method;
pulse-width modulation (e.g., in the case when the irradiated electromagnetic wave is converted by the tissue structures into pulses with measurable pulse durations, from which it is possible to obtain information about the stimulation and/or the tissue properties);
recognition of the change by the application of filters (e.g., to detect the frequency spectrum of the measured electromagnetic waves).

According to a special exemplary embodiment, the electronics unit recognizes the frequency or a frequency spectrum or a frequency shift of the electromagnetic waves measured by the pickup unit through detection of the change as a consequence of a filter effect.

According to one example, the electronics unit is designed to determine the spectral power density in the electromagnetic waves measured by the pickup unit.

Furthermore, according to one aspect of the inventive device, the electronics unit or pickup unit converts the measured electromagnetic wave into an electronic signal and preprocesses it by means of at least one of the following processes:
amplification;
demodulation;
filtering;
AD conversion;
rectification;
determination of the signal strength;
threshold determination;
transformation in the frequency domain (e.g., via a Fourier, Hartley, or wavelet transform)
determination of signal quality (e.g., through determination of the signal-to-noise ratio [SNR]), and/or
determination of signal morphological parameters (e.g., signal amplitude, signal spikes, ratios of signal amplitudes and/or signal spikes, etc.).

According to one exemplary embodiment of the inventive device, the electronics unit or pickup unit converts the measured electromagnetic wave into an electronic signal. Furthermore, the electronics unit analyzes the signal on the basis of at least one of the following processes:
segmentation;
event detection;
determination of periodicity;
determination of the phase position (e.g., determining the phase position between said signal and another picked up signal or a reference signal);
determination of stability (e.g., recognizing the stability of the signal intensity or the stability of a rhythm detected in the signal); or
classification of rhythms; and/or
classification of signal morphological parameters.

According to one exemplary embodiment of the inventive device, the pickup unit has at least one of the following sensors:
a photodiode;
a phototransistor;
a charge-coupled device (CCD) element; and/or
an analog or digital image sensor.

Furthermore, according to one aspect of this invention, the device comprises at least one first and one second actuator, the first and the second actuators emitting electromagnetic waves at different frequencies. The first actuator can be coupled with a housing of the device. Alternatively, the first actuator can be arranged remote from the housing. The first actuator can be connected with the pickup unit.

According to one exemplary embodiment, the device has electrical stimulation means. According to one aspect of the invention, the device is designed to emit electromagnetic waves to cardiac tissue or to nerve tissue in the spinal cord or muscle tissue.

According to exemplary embodiments, the at least first actuator comprises LEDs. In a special implementation, the actuator comprises a filter (e.g., polarizing filter). According to one exemplary embodiment, the emission characteristics (i.e., direction, intensity, frequency, duration of the emission) are programmable by the controller. If the device is an implant, said programming can occur before and also after implantation.

According to one exemplary embodiment, the device comprises a fixation device. The fixation device is designed so that actuators and/or sensors are fastened to it in such a way that the electromagnetic radiation penetrates the tissue.

The inventive device can be implanted by means of a controllable positioning aid (e.g., a controllable catheter, steerable sheaths, over-the-wire [OTW] technique, etc.). The device can be positioned using imaging techniques (e.g., X-ray imaging, computed tomography, magnetic resonance imaging, ultrasound, impedance tomography).

The inventive idea proposes a method for controlling a device that is implantable in the human or animal body. The method has at least the steps:

Inducing a measurement of electromagnetic waves in the frequency range $10^{13}$-$10^{20}$ Hz; and Inducing a detection of whether the electromagnetic waves were emitted from genetically manipulated tissue.

Other features which are considered as characteristic for the invention are set forth in the appended claims.

Although the invention is illustrated and described herein as embodied in a device and method to activate cell structures by means of electromagnetic energy, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 8 schematic representation of an embodiment of an inventive implantable stimulator;

FIG. 9 implantable stimulator according to FIG. 8 with an alternative fixation device;

FIG. 8b schematic representation of an embodiment of the inventive stimulation device with a defibrillation function;

FIG. 9b implantable stimulator according to FIG. 8b with an alternative fixation device;

FIG. 23 table showing exemplary combinations of stimulation and shock vectors between right ventricle, housing of the stimulation device, and right atrium;

DETAILED DESCRIPTION OF THE INVENTION

Figure 1:
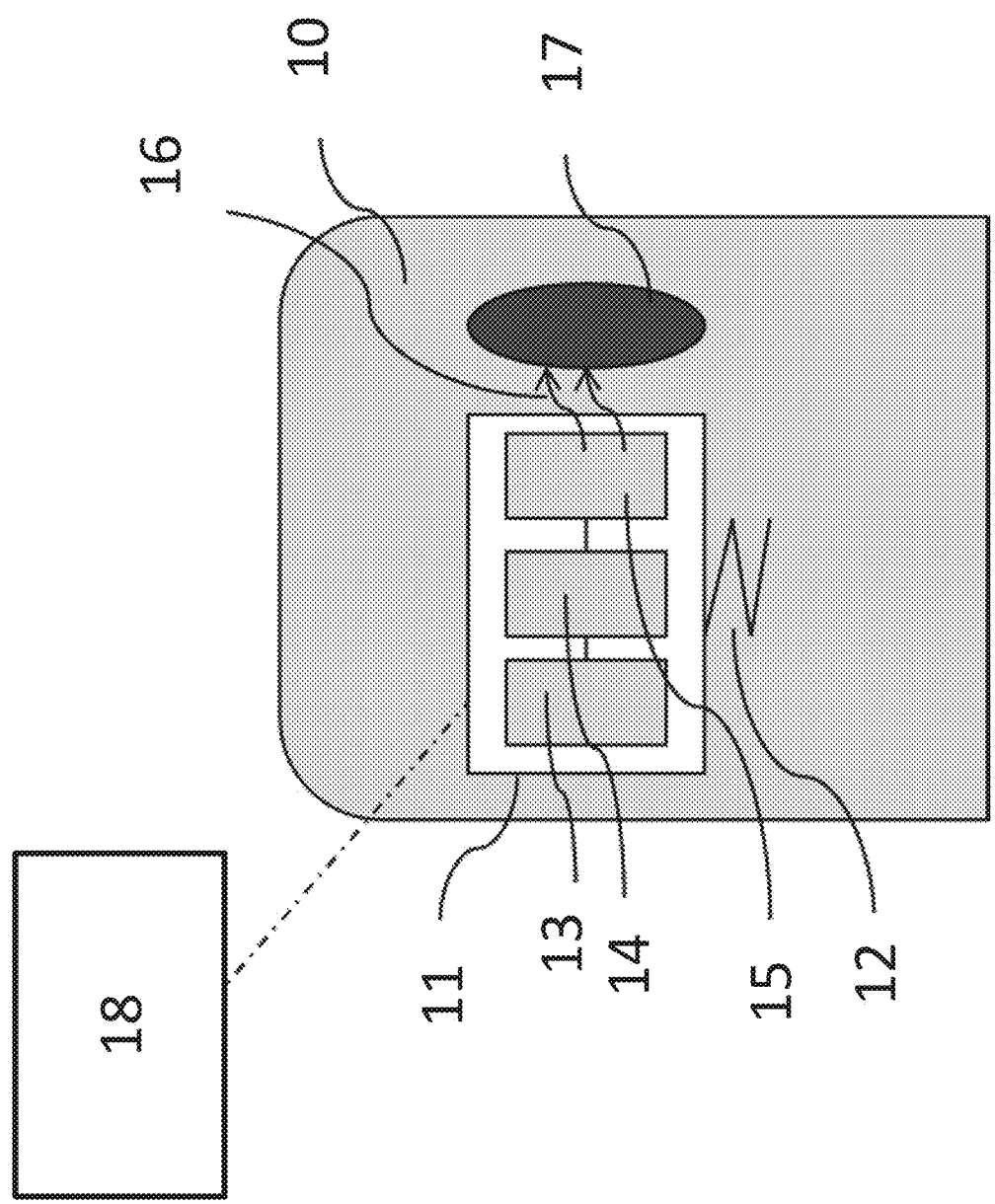
FIG. 1 schematic representation of a exemplary embodiment of the inventive stimulation device in the implanted state with an external device.

Referring now to the figures of the drawing in detail and first, particularly, to FIG. 1 thereof, there is shown an implantable stimulator according to the invention. The stimulator is implanted into the body tissue of a patient 10 and comprises a hermetically sealed housing 11. Here this housing is anchored in the body tissue by means of a fixation device 12. The implant housing 11 comprises an energy source 13, a controller 14, and an actuator 15, the latter being designed to be able to deliver electromagnetic radiation 16, e.g., in the range of visible light, to a body tissue 17 that has been pretreated beforehand, for example by means of genetic, especially optogenetic manipulation and, for example, to evoke an action potential, i.e., to trigger a stimulation by means of electromagnetic radiation. In addition, the implant can be read out and/or programmed by means of an external device 18, e.g., a telemetry unit.

Figure 2:
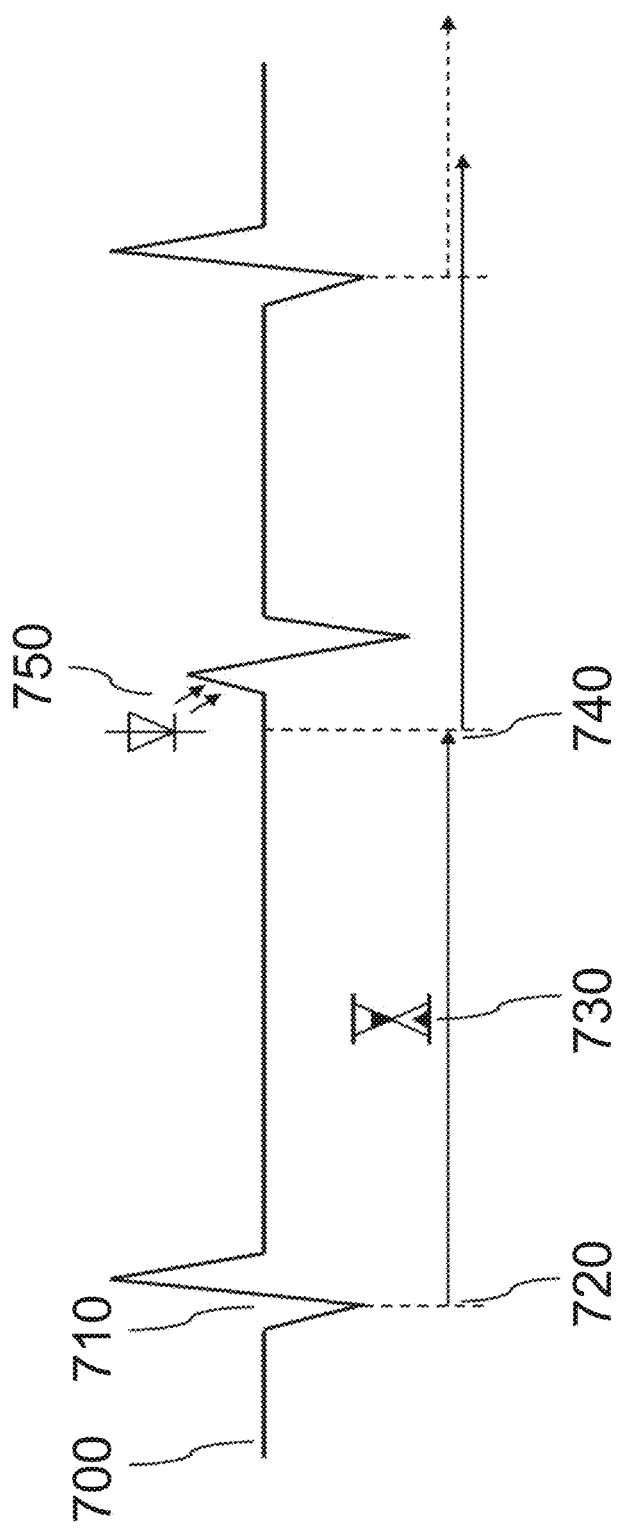
FIG. 2 schematic representation of a method for treating bradycardia by means of optical stimulation for at least one exemplary embodiment of the inventive stimulation device.

FIG. 2 illustrates a method for treatment of bradycardia by means of stimulation of genetically manipulated tissue, preferably optogenetically manipulated tissue. The schematized ECG 700 first shows a regular heartbeat 710 in the form of an intrinsic QRS complex. In the proposed process, this QRS complex is first recorded 720 and then a time interval 730 is started, which corresponds to an expected heart rate. If the expected interval 740 passes without another intrinsic QRS complex being recorded, then an optical stimulation 750 is triggered, which triggers a stimulated QRS complex in the preferably optogenetically pretreated myocardial tissue.

Figure 3:
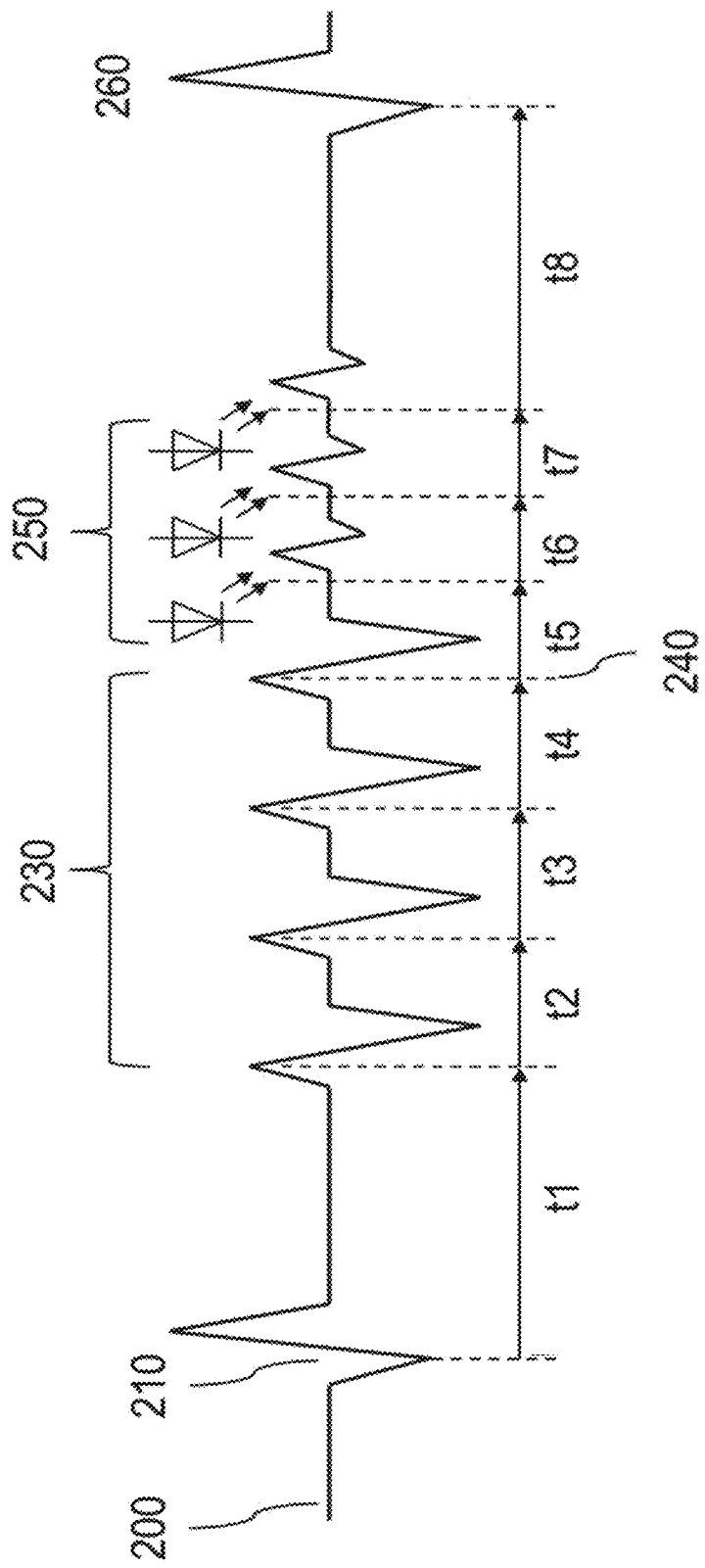
FIG. 3 schematic representation of a method for treating a tachycardia arrhythmia in the form of a ventricular or atrial tachycardia for at least one exemplary embodiment of the inventive stimulation device.

FIG. 3 illustrates a method for treatment of a tachycardia arrhythmia in the form of a ventricular or atrial tachycardia. The schematized ECG 200 first shows a regular contraction 210 of a ventricle. To monitor the cardiac rhythm, each of these contractions is recorded and starts a time measurement until the next recorded contraction (t1 . . . t8). In the example shown, now a too rapid heart rate begins in the form of tachycardia 230, which is first recorded over a few heartbeats and confirmed 240. After confirmation 240, a predetermined optical stimulation sequence 250 is delivered to the preferably pretreated myocardium, causing a series of stimulated excitations which, as a rule, end the tachycardia and restore a regular rhythm 260.

Figure 4:
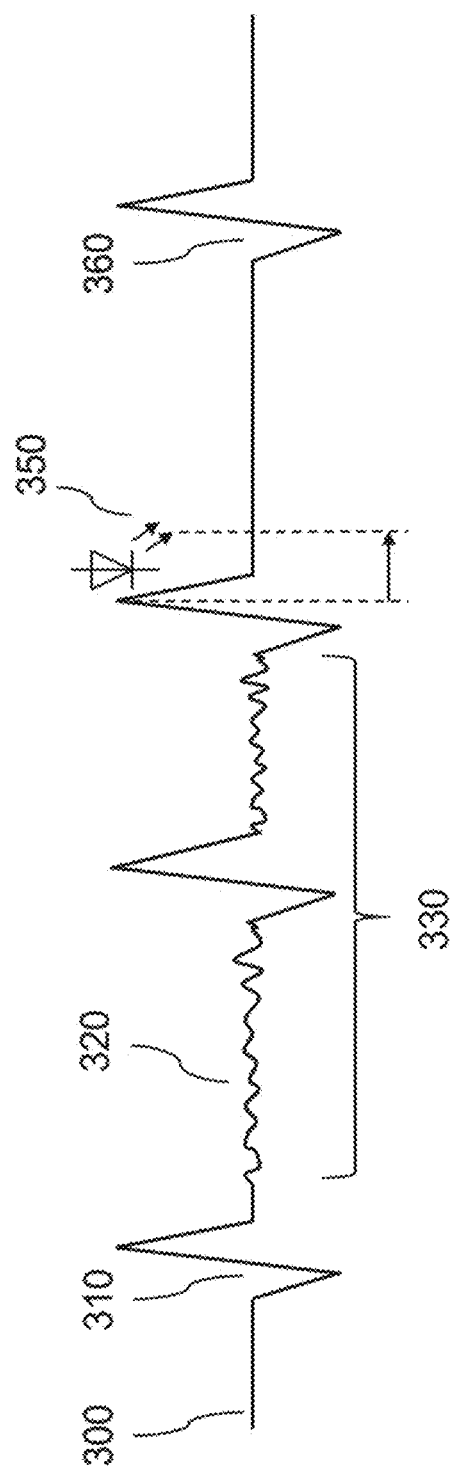
FIG. 4 schematic representation of a method for treating atrial fibrillation for at least one exemplary embodiment of the inventive stimulation device.

FIG. 4 illustrates a method for treatment of atrial fibrillation. The schematized ECG 300 first shows a QRS complex in a sinus rhythm 310. Then, atrial fibrillation 320 spontaneously begins. This is first recorded and confirmed 330. Once this atrial fibrillation 320 is confirmed, an optical stimulation 350 is delivered to the atria of the pretreated heart, however it is synchronized with and offset in time to a QRS complex (cardioversion). This terminates the atrial fibrillation and restores a regular sinus rhythm 360.

Figure 5:
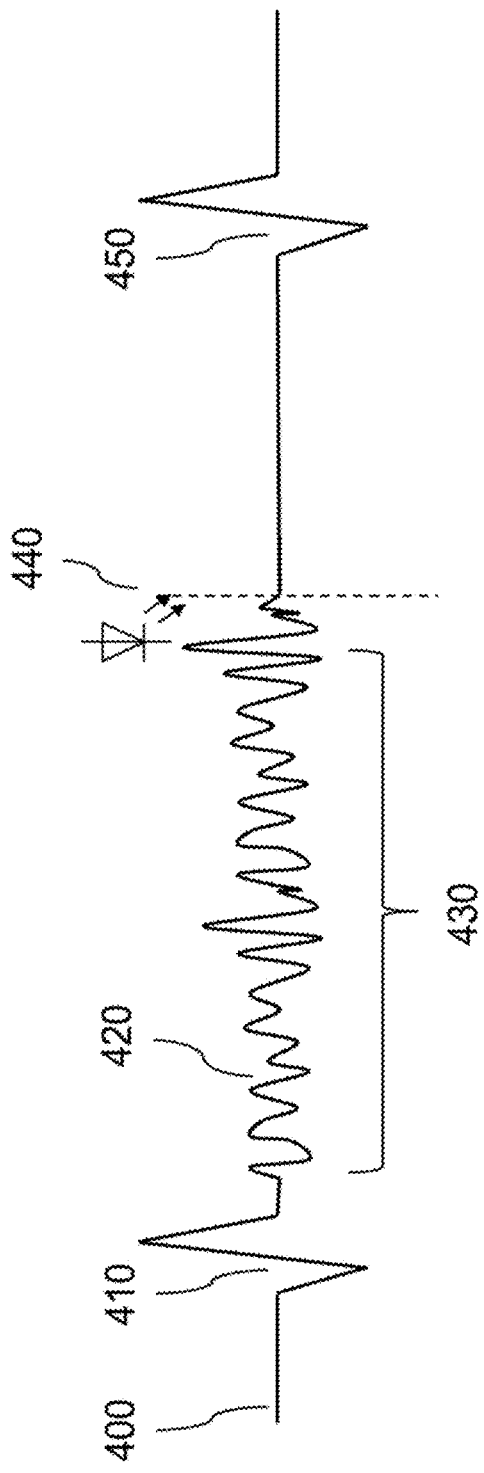
FIG. 5 schematic representation of a method for treating ventricular fibrillation for at least one exemplary embodiment of the inventive stimulation device.

FIG. 5 illustrates a method for treatment of ventricular fibrillation. The schematized ECG 400 first shows a QRS complex in a sinus rhythm 410. Then, ventricular fibrillation 420 spontaneously begins, which is first recorded and then confirmed 430. Once this ventricular fibrillation 420 is confirmed, a large-area optical stimulation 440 is triggered in the area of the preferably optogenetically pretreated ventricles, terminating the ventricular fibrillation and restoring a sinus rhythm 450.

Figure 6:
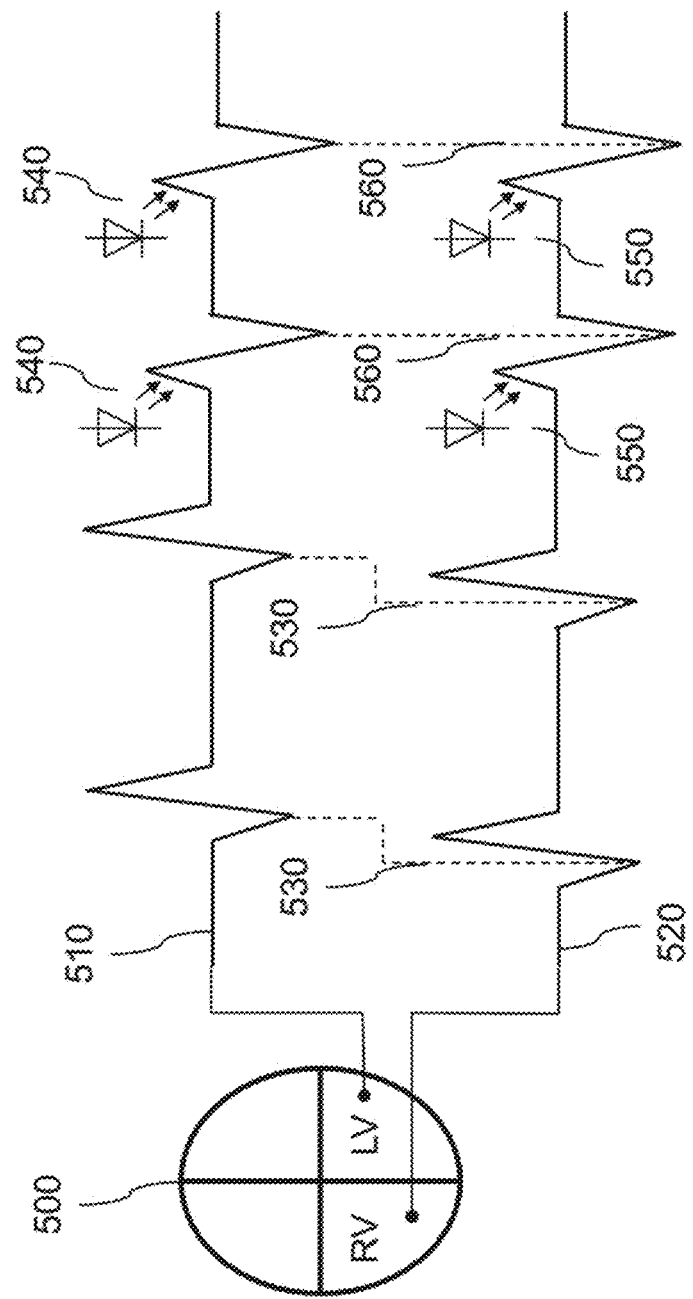
FIG. 6 schematic representation of a method for application of cardiac resynchronization therapy by means of electromagnetic waves for at least one exemplary embodiment of the inventive stimulation device.

FIG. 6 illustrates a cardiac resynchronization method for stimulation of genetically manipulated tissue, preferably optogenetically manipulated tissue. This figure schematically shows the intracardiac ECG leads from both ventricles of the heart 500: the left ventricle (LV; 510) and the right ventricle (RV, 520). The ECG leads first show a time delay 530 in the left ventricular heartbeats with respect to the right ventricular heartbeats. This offset is the expression of a so-called left bundle branch block, which in the case of advanced structural damage to the heart muscle requires therapy in the form of a resynchronization of both ventricles. Here this resynchronization is performed by means of simultaneous or quasi-simultaneous optical stimulation 540, 550 of both ventricles of the heart, permanently producing a mechanical contraction 560 of both ventricles at the same time.

Figure 7:
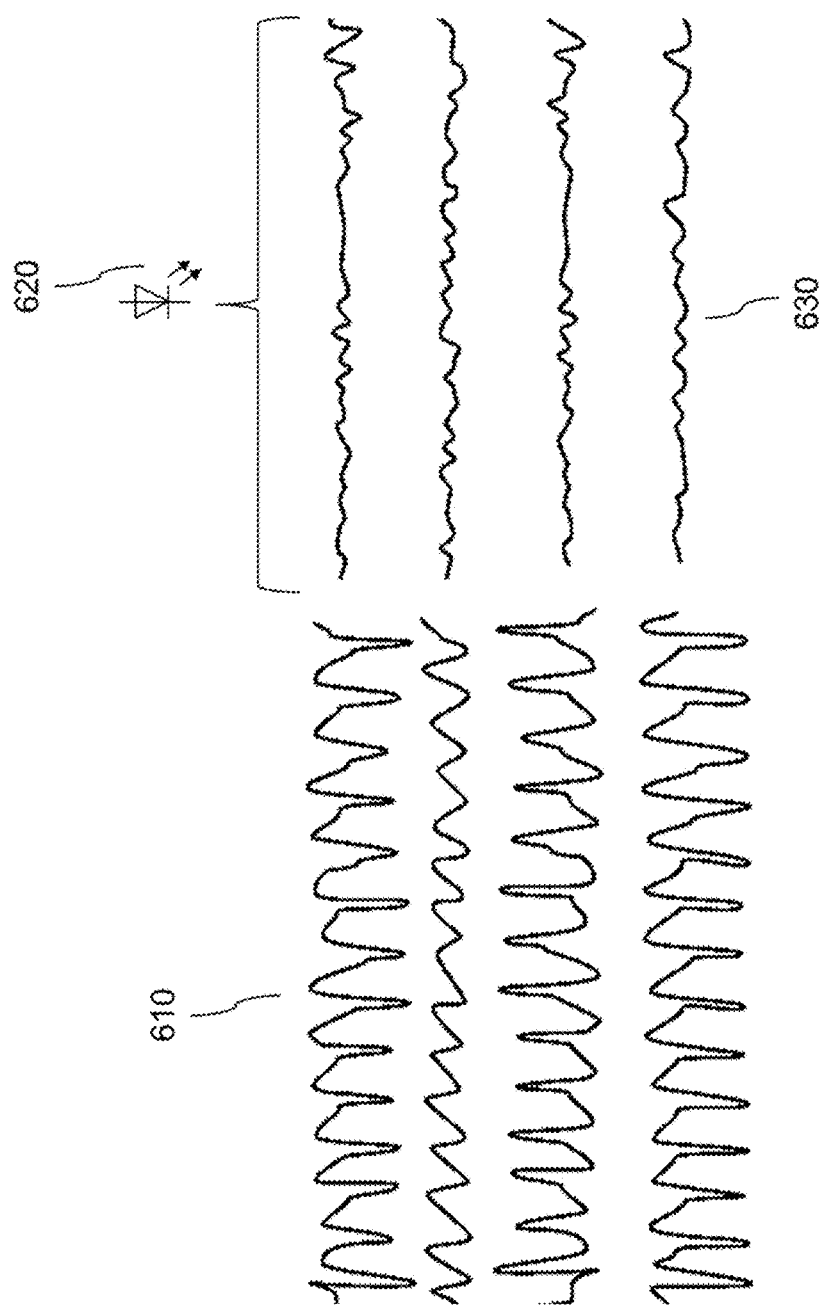
FIG. 7 schematic representation of a neurostimulation method by means of electromagnetic waves for at least one exemplary embodiment of the inventive stimulation device.

FIG. 7 illustrates an example of neurostimulation of genetically manipulated tissue, preferably optogenetically manipulated tissue. In the example shown, the left side depicts an EEG detail 610 of an epileptic seizure. For treatment, an optical stimulation sequence 620 is delivered to one or more preferably optogenetically pretreated brain regions, to bring about termination 630 of this epileptic seizure. The method of optical neurostimulation shown here is intended to serve as a representative application illustrating all others, e.g., spinal cord stimulation, other applications of deep brain stimulation or cortical stimulation, insulated nerve stimulation, muscle stimulation, etc.

FIG. 8 shows a possible embodiment of an inventive implantable stimulator. This stimulator consists of a battery 81 and implant electronics 82, both of which are in a hermetically sealed housing, the implant electronics 82 comprising the components of the block diagram shown in FIG. 10. On the bottom of the housing there is a light source 83 that is also hermetically sealed, however it is sealed in such a way that the frequency spectrum of this light source can penetrate the hermetic sealing and excite the target tissue (here myocardium 85). Here the implant is fixed in the myocardium 85 with a helix 84.

FIG. 9 shows the implantable stimulator from FIG. 8 consisting of a battery 81 and implant electronics 82, however with an alternative fixation device 94 in the form of barbs made, e.g., of nitinol, on the side. On the bottom of the housing there is a light source 93 that is hermetically sealed in such a way that the frequency spectrum of this light source can penetrate the hermetic sealing and excite the target tissue (here myocardium 95).

Figure 10:
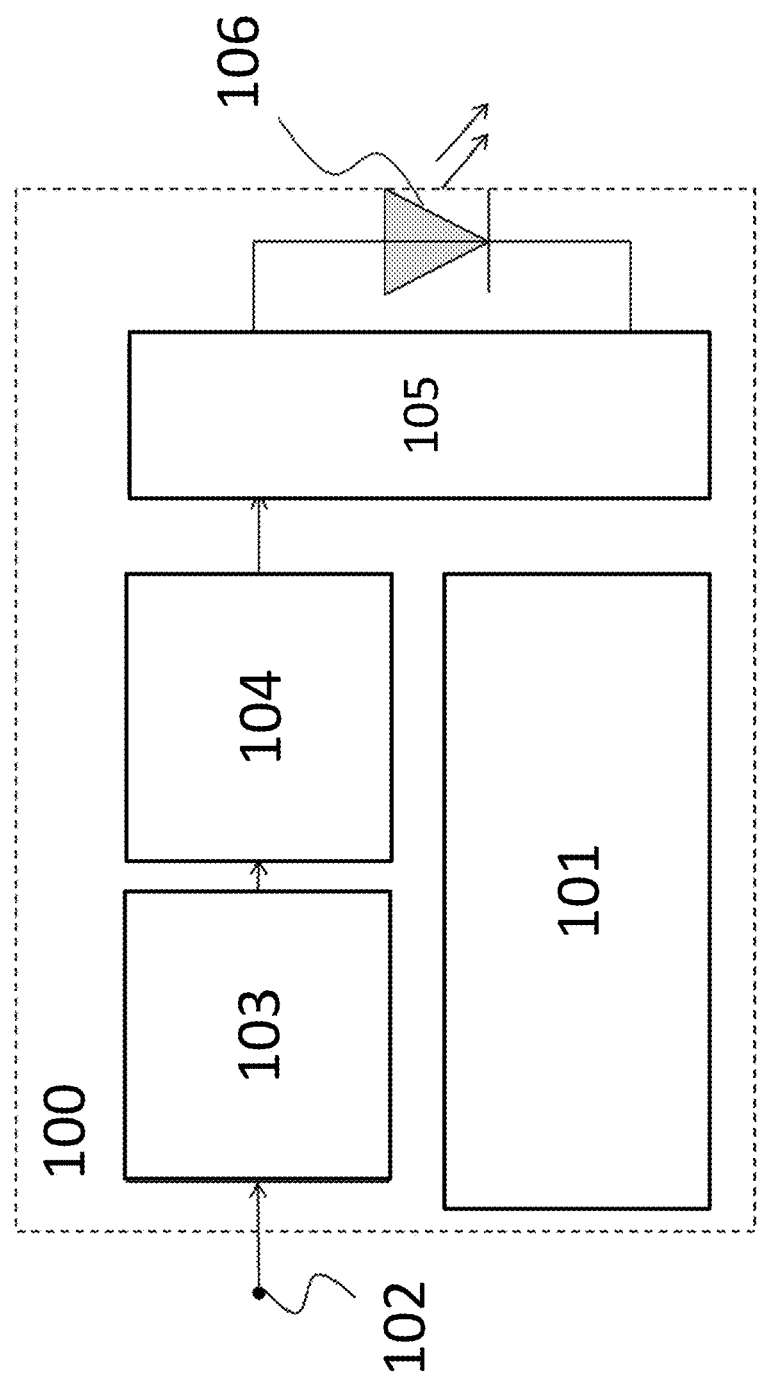
FIG. 10 block diagram of the implantable stimulator according to one exemplary embodiment of the invention.

FIG. 10 shows the block diagram of the implantable stimulator 100. The latter comprises an energy source 101, a sensor interface 102 for detection of a feature representing a heartbeat, connected with a detection unit 103, which in turn signals the detection of heartbeats to the connected controller 104. This controller 104 is connected with a therapy generator 105, which upon receipt of a trigger signal from the controller 104 excites an LED 106 that is connected to the therapy generator and thus emits a light signal that stimulates the myocardial tissue. The therapy generator 105 can vary the intensity, duration, signal form, and color of the light signal.

Figure 8A:
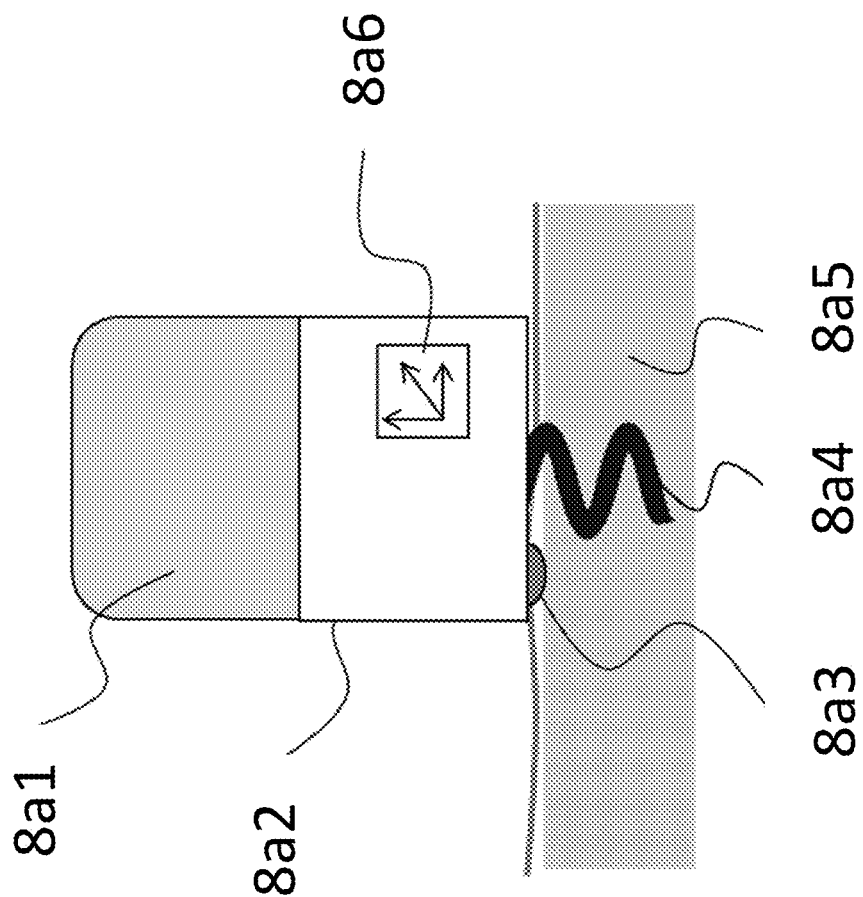
FIG. 8a schematic representation of an embodiment of the inventive stimulation device with control of the success of the therapy.

FIG. 8a shows a possible embodiment of an inventive implantable stimulator with control of the success of the therapy. This stimulator consists of a battery 8a1 and implant electronics 8a2, both of which are in a hermetic housing, the implant electronics 8a2 comprising the components of the block diagram from FIG. 9a. On the bottom of the housing there is a light source 8a3 that is also hermetically sealed, however it is sealed in such a way that the frequency spectrum of this light source can penetrate the hermetic sealing and excite the target tissue (here myocardium 8a5). Here the implant is fixed in the myocardium 8a5 with a helix 8a4. In this exemplary embodiment, the implant electronics 8a2 additionally comprise a 3D accelerometer 8a6, which is used to control of the success of the therapy by evaluating, after every optical stimulation, whether an acceleration of the implant fixed to the myocardium has been detected. In this case, the stimulation is considered effective, since contraction of the cardiac tissue leads to acceleration. If the acceleration fails to appear, the stimulation is considered ineffective and is repeated, e.g., with higher amplitude, or alternatively an ineffective stimulation is signaled to a remote monitoring system.

Figure 9A:
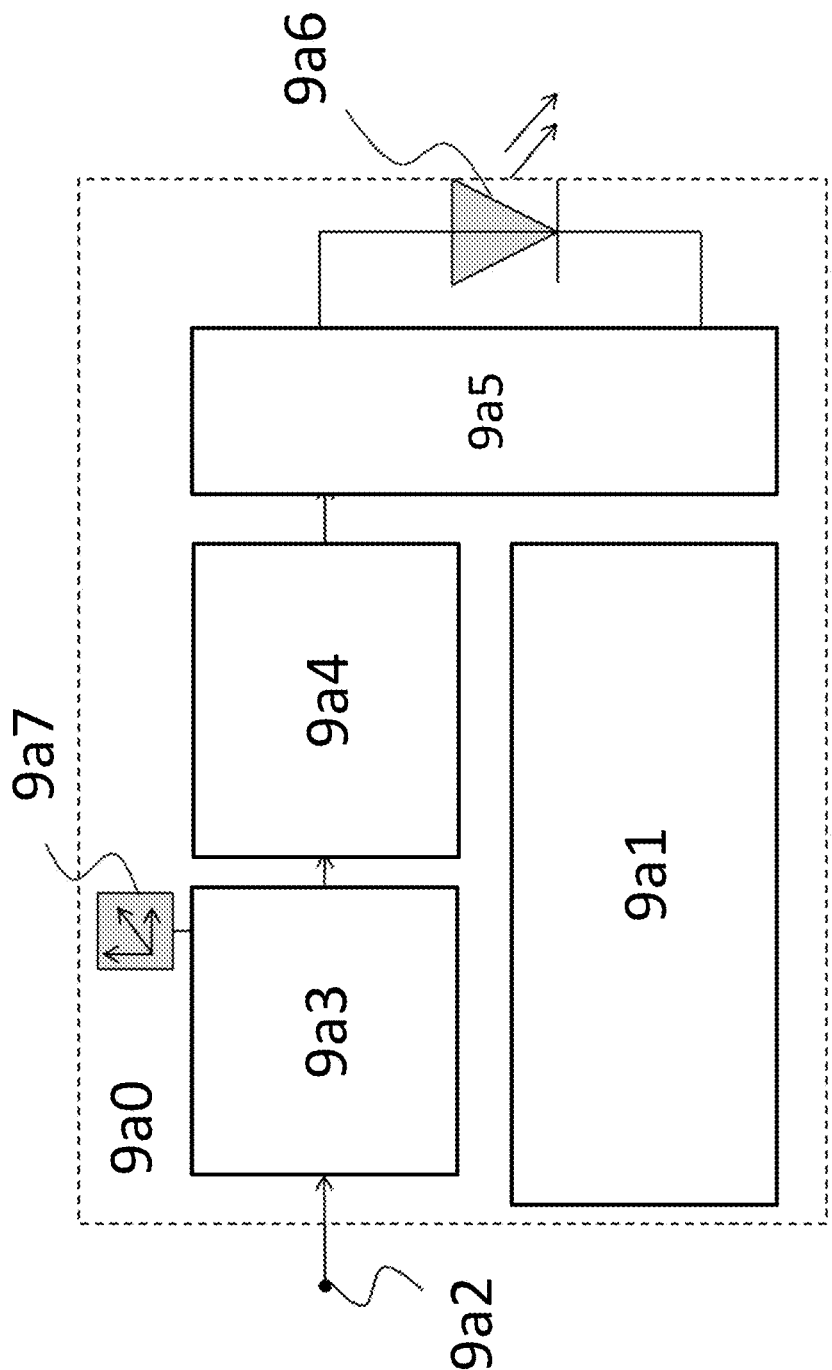
FIG. 9a block diagram of the inventive stimulation device according to one exemplary embodiment.

FIG. 9a shows the block diagram of the implantable stimulator 9a0. The latter comprises an energy source 9a1, a sensor interface 9a2 for detection of a feature representing a heartbeat, connected with a detection unit 9a3, which in turn signals the detection of heartbeats to the connected controller 9a4. This controller 9a4 is connected with a therapy generator 9a5, which upon receipt of a trigger signal from the controller 9a4 excites an LED 9a6 that is connected to the therapy generator and thus emits a light signal that stimulates the myocardial tissue. The therapy generator 9a5 can vary the intensity, duration, signal form, and color of the light signal.

The detection unit 9a3 is further connected with a 3D accelerometer 9a7, which is used to control the success of the therapy by evaluating, after every optical stimulation, whether an acceleration of the implant fixed to the myocardium has been detected. In this case, the stimulation is considered effective, since contraction of the cardiac tissue leads to acceleration. If the acceleration fails to appear, the stimulation is considered ineffective and is repeated, e.g., with higher intensity, duration, an alternative signal form, or another color.

Figure 10A:
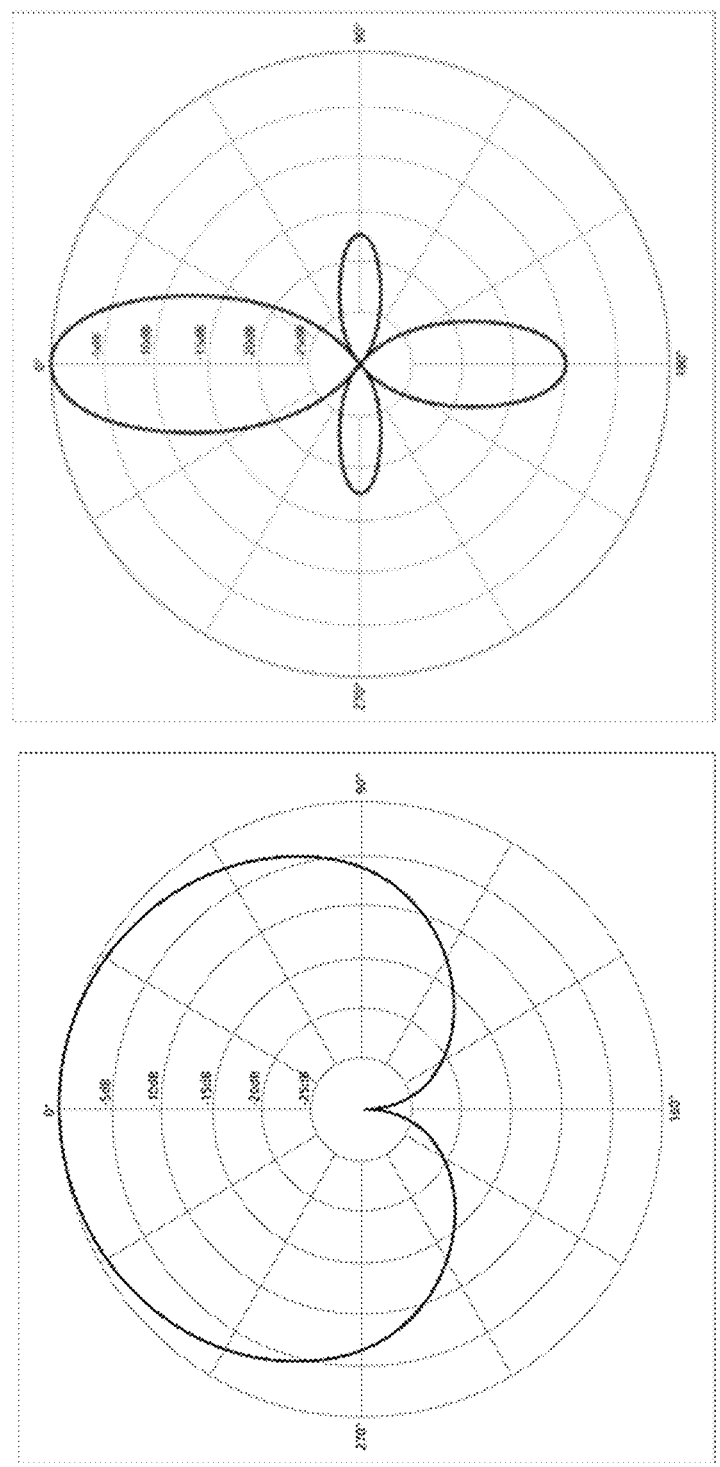
FIG. 10a shows an example of two-dimensional characteristics of electromagnetic radiators with spatially selective effect.

FIG. 10a shows examples of two-dimensional characteristics of electromagnetic radiators with spatially selective effect.

FIG. 8b shows a possible embodiment of an inventive implantable defibrillator. This defibrillator consists of a high-power LED 8b1 and encapsulated implant electronics along with an energy source 8b2, both of which are in a hermetically sealed housing. The implant electronics comprising the components of the block diagram shown in FIG. 3. On the bottom of the housing there is another local light source 8b3, which is arranged and dimensioned in such a way that this local light source 8b3 can only trigger a local depolarization in the pretreated myocardium 8b5. Here the implant is fixed in the myocardium 8b5 with a helix 8b4. The high-power LED 8b1 is dimensioned so that it can, for the purpose of defibrillation, "shine through" almost the entire heart, so that a simultaneous depolarization of all excitable myocardial cells at the moment of defibrillation is possible.

FIG. 9b shows the implantable stimulator from FIG. 8b, however with an alternative fixation device 9b4, in the form of nitinol barbs on the side. On the bottom of the housing there is a light source 9b3 that is hermetically sealed in such a way that the frequency spectrum of this light source can penetrate the hermetic sealing and excite the target tissue (here myocardium 9b5).

Figure 10B:
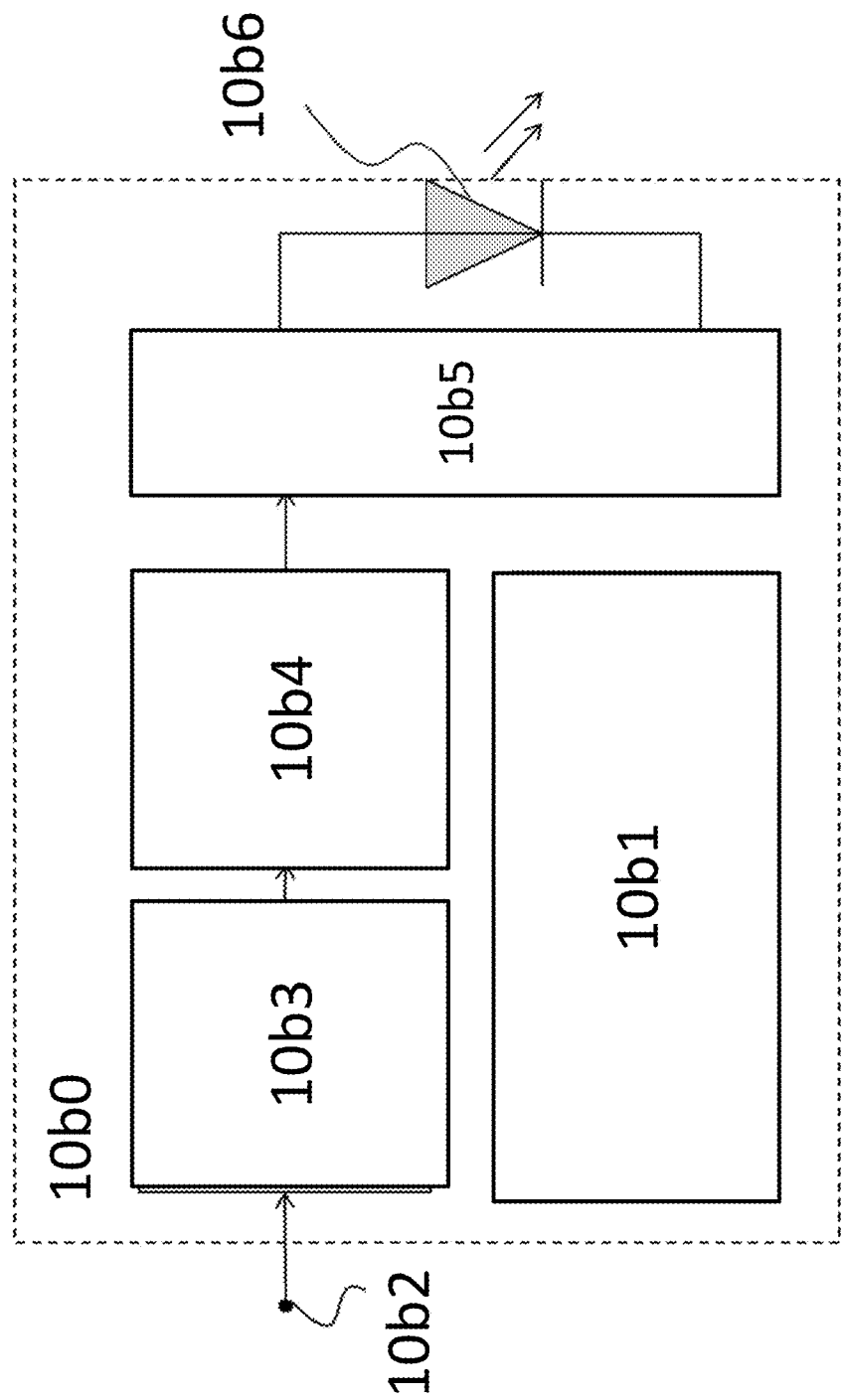
FIG. 10b block diagram of the inventive stimulation device according to a exemplary embodiment according to FIG. 8b.

FIG. 10b shows the block diagram of the implantable stimulator 100 according to FIG. 8b. The latter comprises an energy source 10b1, a sensor interface 10b2 for detection of a feature representing a heartbeat, connected with a detection unit 10b3, which in turn signals the detection of heartbeats to the connected controller 10b4. This controller 10b4 is connected with a therapy generator 10b5, which upon receipt of a trigger signal from the controller 10b4 excites an LED 10b6 that is connected to the therapy generator and thus emits a light signal that stimulates the myocardial tissue. The therapy generator 10b5 can vary the intensity, duration, signal form, and color of the light signal.

Figure 11:
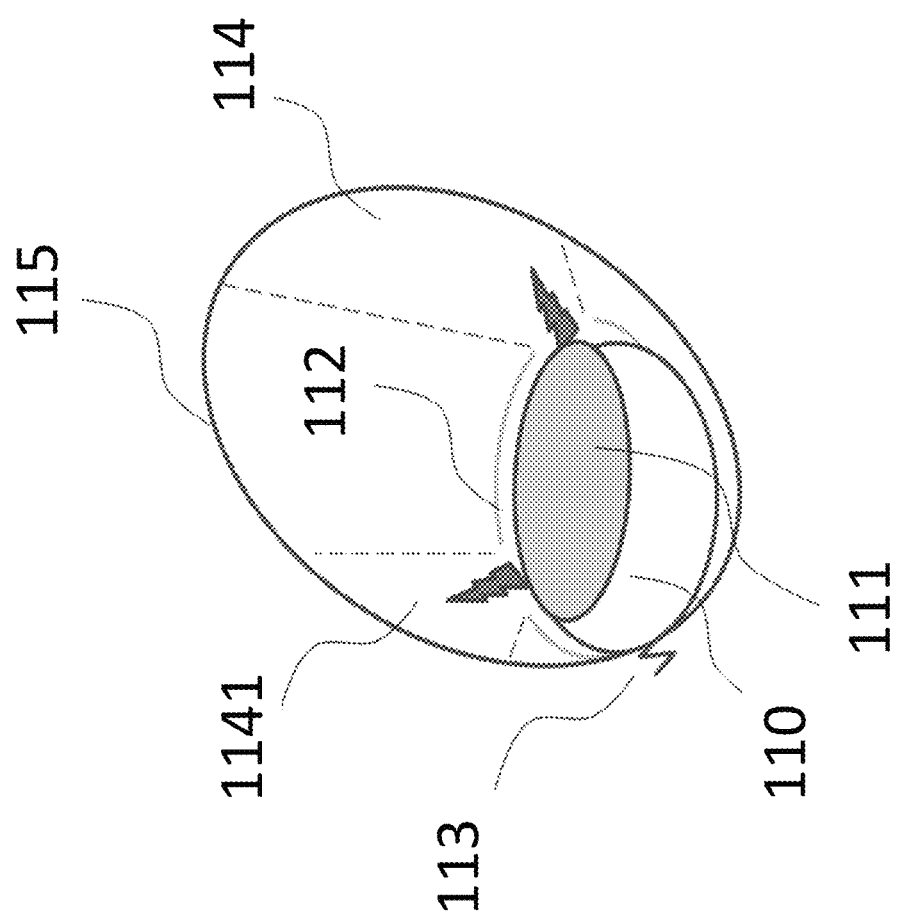
FIG. 11 through 14 show implementations of the inventive stimulation system with a selector that is designed to select the area of the said tissue for the stimulation according to embodiments.

FIG. 11 shows a typical implementation. The implant 110 is fastened to organ tissue by means of a fixation device 113 and has an electromagnetic radiator 111 that is masked by means of the masking device or mask 112, in order to have electromagnetic energy radiated onto the treated tissue 115 only within the effective cones 114 and 1141.

Figure 12:
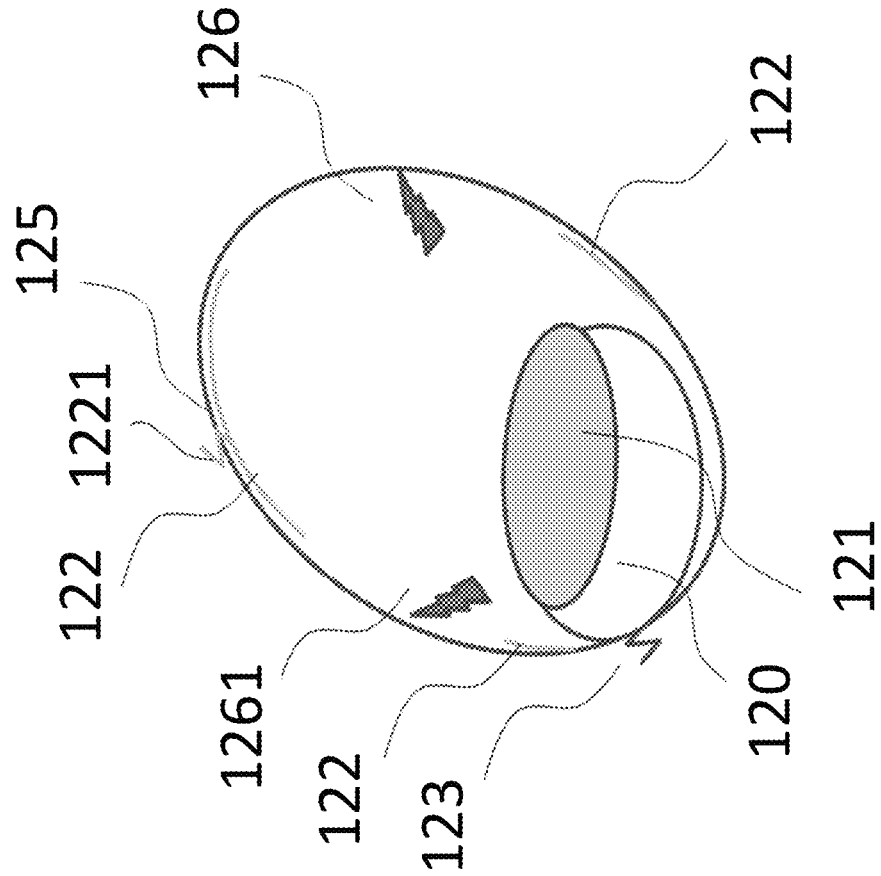

FIG. 12 discloses the implementation in which the masking device or mask 122 represents a second unit and is fastened by means of a fixation device 1221 independently of the implant, in order to prevent the penetration of electromagnetic energy into the covered tissue regions. The implant 120 is fastened to the organ tissue by means of a fixation device 123 and has an electromagnetic radiator 121 that is masked by means of the mask 122. The therapy acts on the treated tissue 125 only in the unmasked regions 126 and 1261.

Figure 13:
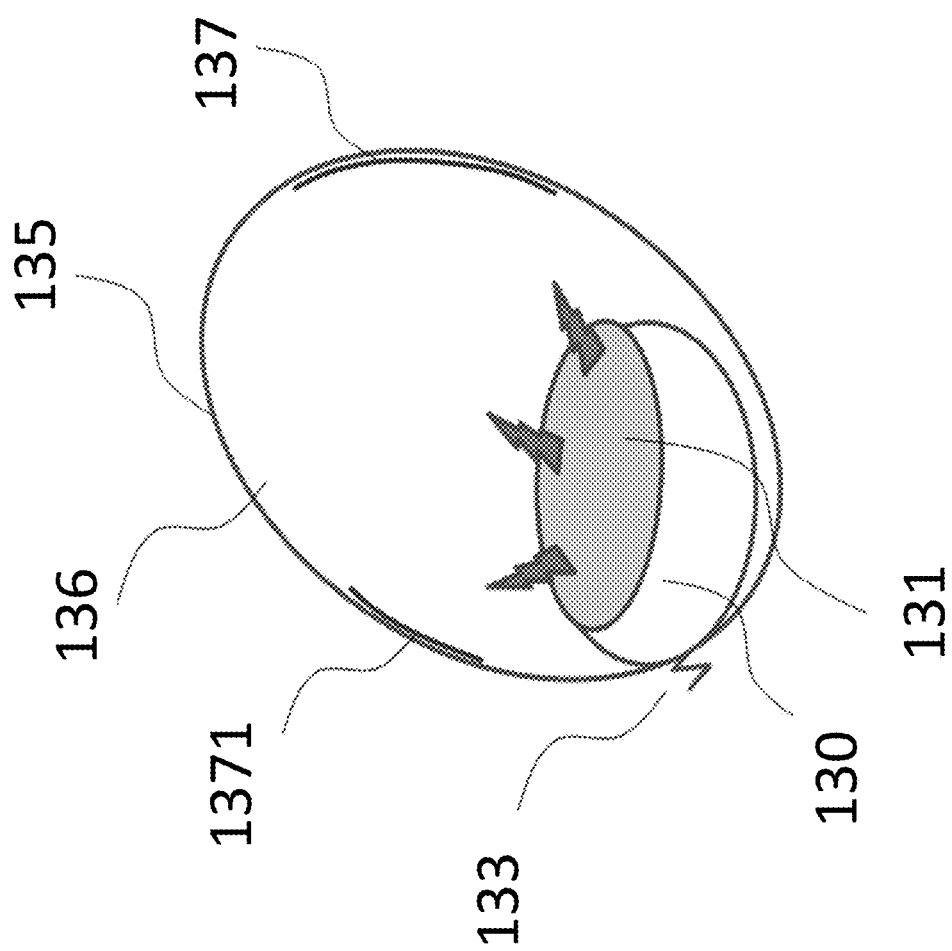

FIG. 13 shows an implementation with locally pretreated tissue. Although the effective range 136 of the radiation covers all the tissue 135, the radiation only acts on the tissue in the regions 137 and 1371. The implant 130 is fastened to the organ tissue by means of a fixation device 133 and has an electromagnetic radiator 131. The therapy acts on the treated tissue 135 only in the pretreated regions 137 and 1371.

Figure 14:
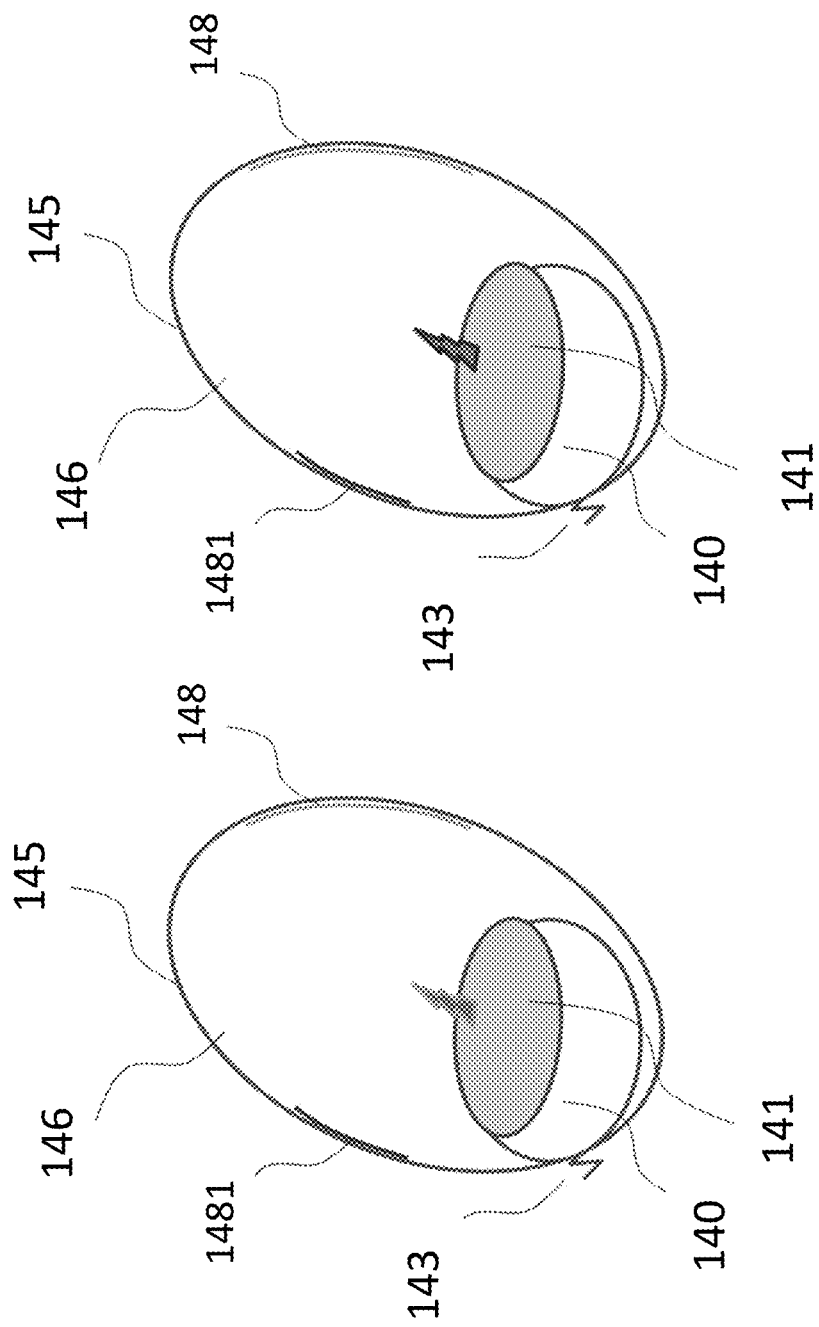

FIG. 14 discloses a solution with tissue that reacts in a locally frequency-specific (or polarization-specific) manner or is pretreated to do so. Depending on the frequency (band) or polarization of the radiator, only the one 148 or the other 1481 region shows an effect. Although the effective range 146 of the radiation covers all the tissue 145, the radiation only acts on the tissue in the regions 148 and 1481. The implant 140 is fastened to the organ tissue by means of a fixation device 143 and has an electromagnetic radiator 141.

Figure 15:
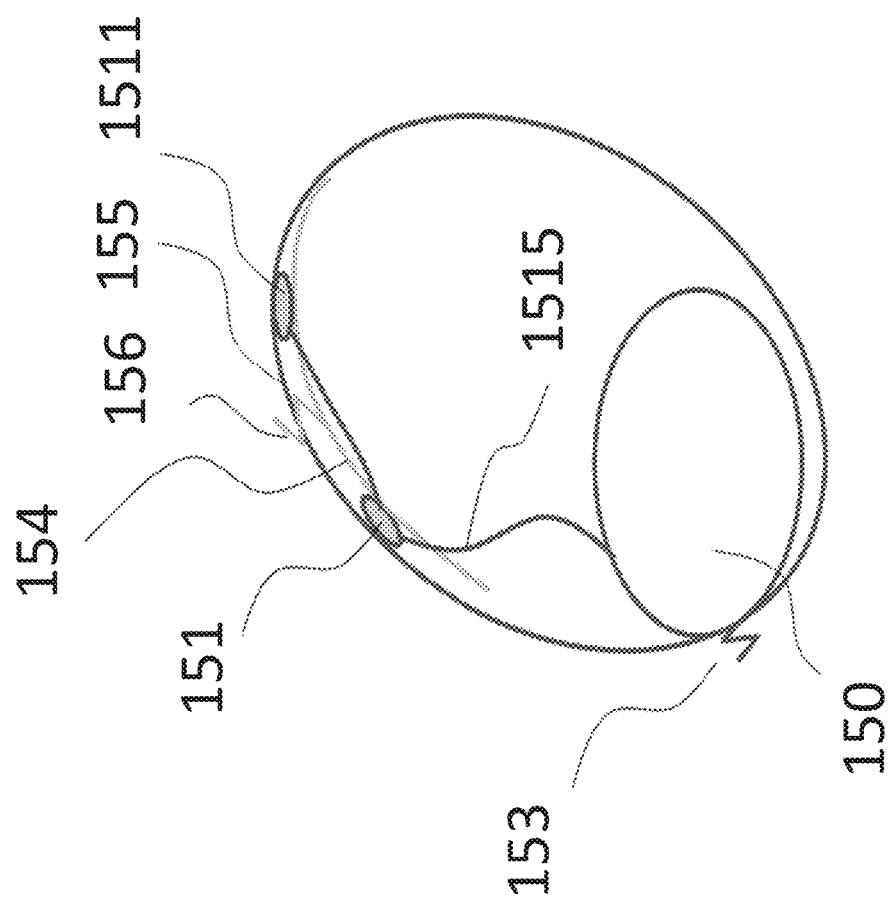
FIG. 15 implementation of the inventive stimulation system with a selector that is designed to select the area of the said tissue for the stimulation, the stimulation system having supports.

FIG. 15 shows a solution with radiators 151 and 1511 that lie distal of the implant housing and that are either put on the treated tissue directly (not shown) or by means of a support 154 with a fixation 156. The support also assumes the role of a mask and shades the rest of the organ. The radiators are supplied through a lead 1515 from the implant 150. Alternatively, the implant itself can assume the role of a support. Then, the radiators are fastened directly to the housing. The implant 150 is fastened to the organ tissue by means of a fixation device 153.

Figure 16:
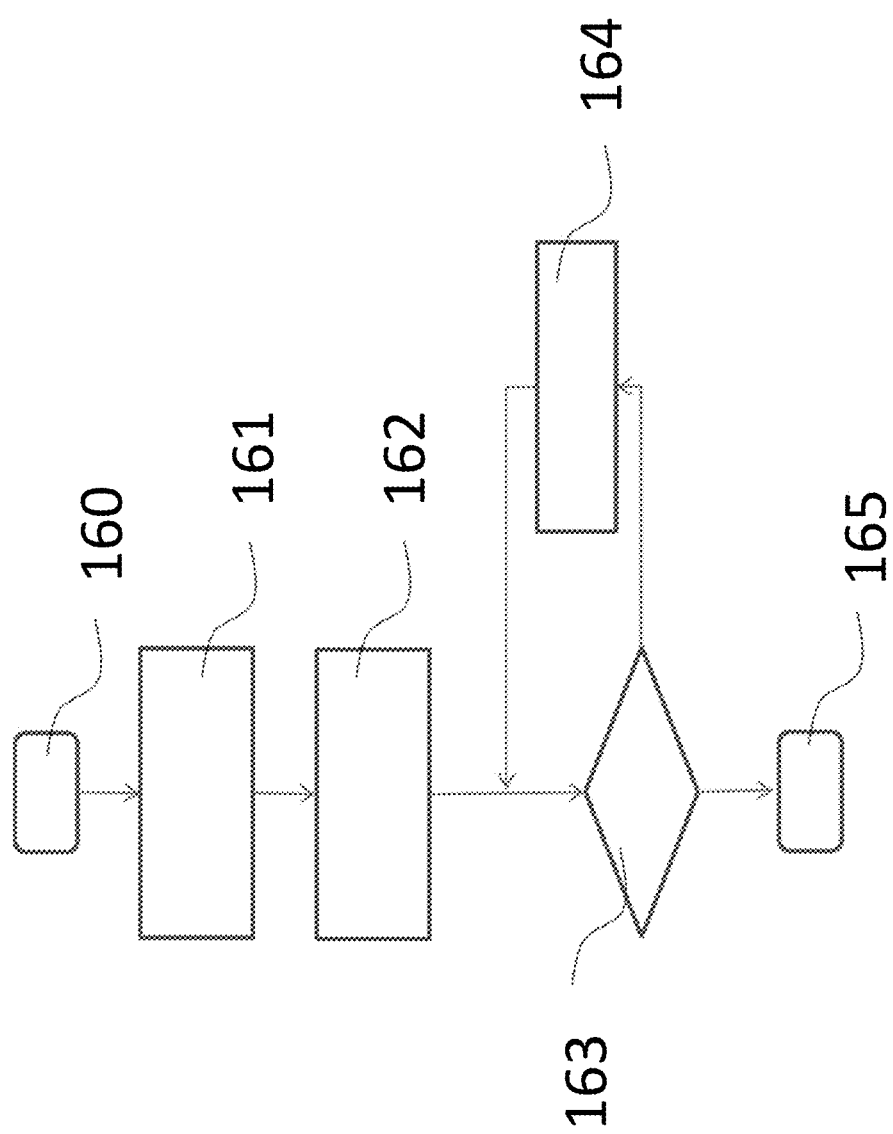
FIG. 16 flowchart of the method for the inventive stimulation system according to exemplary embodiments.

FIG. 16 shows the flowchart of the method for the inventive stimulation system according to exemplary embodiments. After the start 160, the pretreatment 161 is performed, followed by the implantation and fastening of the stimulator 162. After that, the test 163 of the effectiveness of the therapy is carried out. If the test is not successful, the process is improved in step 164. Otherwise, the method is ended (165).

Figure 17:
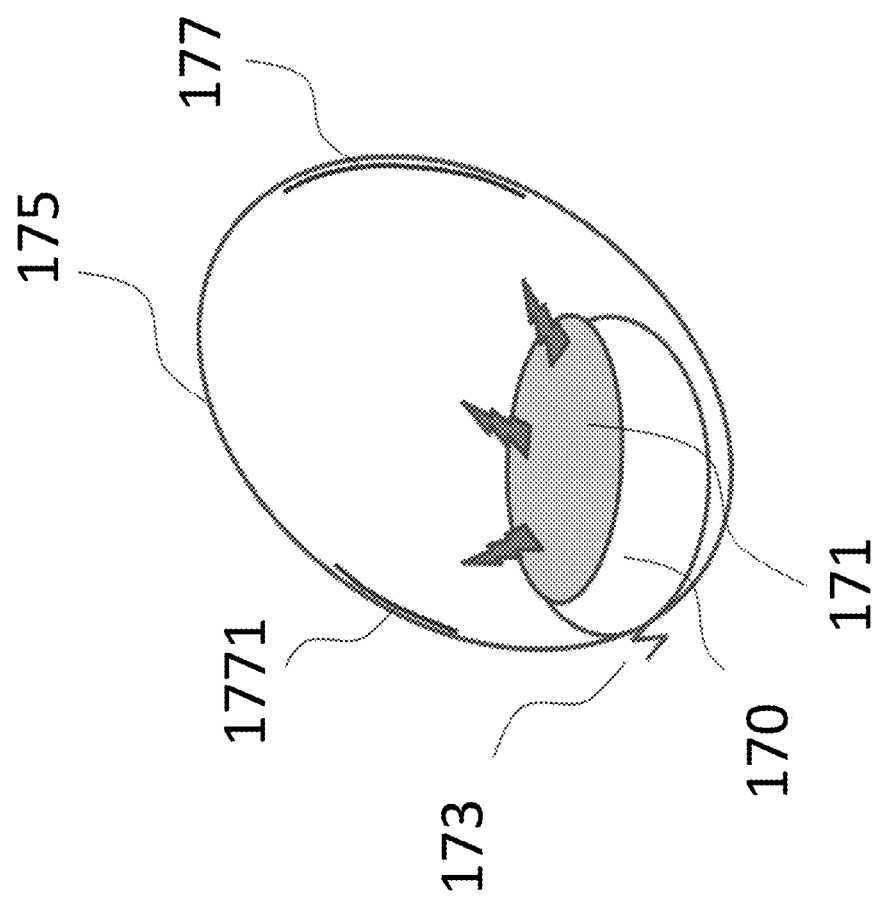
FIG. 17 schematic representation of the local pretreatment to produce sensitive areas for electromagnetic radiation.

FIG. 17 shows the tissue 175 with the pretreated areas 177 and 1771. The stimulator 170 with electromagnetic actuator 171 is fastened to the tissue by means of the fixation 173.

Figure 18:
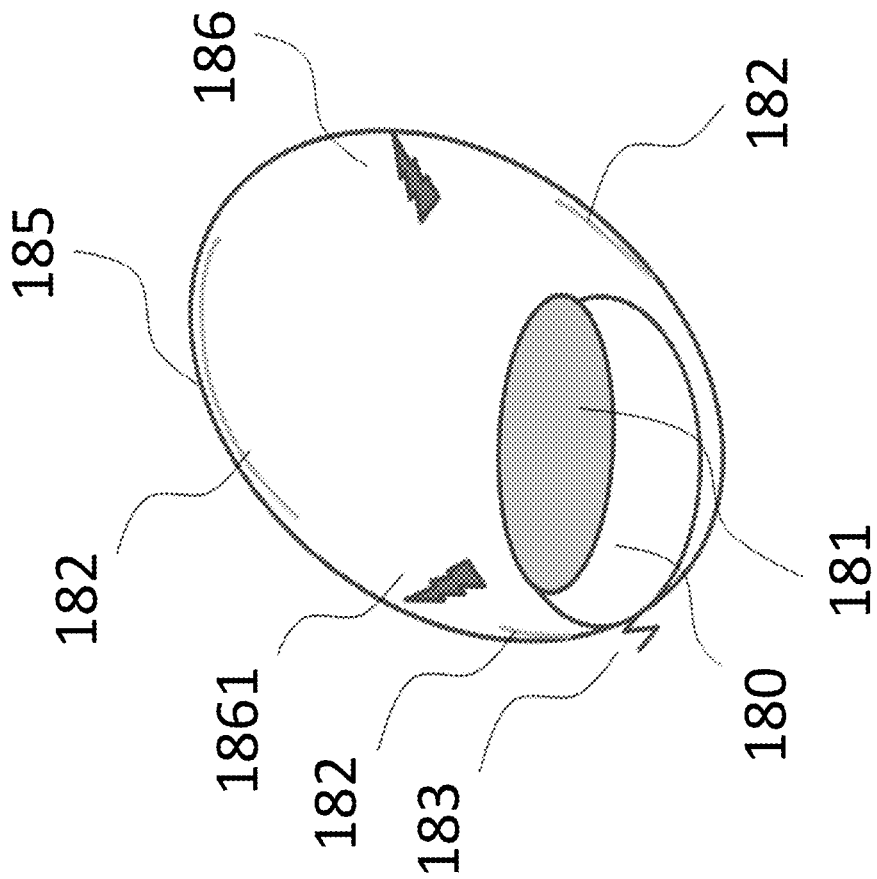
FIG. 18 schematic representation of the local pretreatment to mask possibly sensitive areas for electromagnetic radiation.

FIG. 18 shows the tissue 185 with the areas 182 that have been masked by pretreatment. Thus, only the areas 186 and 1861 are stimulable by the radiation that is output from the actuator 181. The implant 180 is fastened to the organ tissue by means of a fixation device 183 and has an electromagnetic radiator 181.

Figures 19A, 19B:
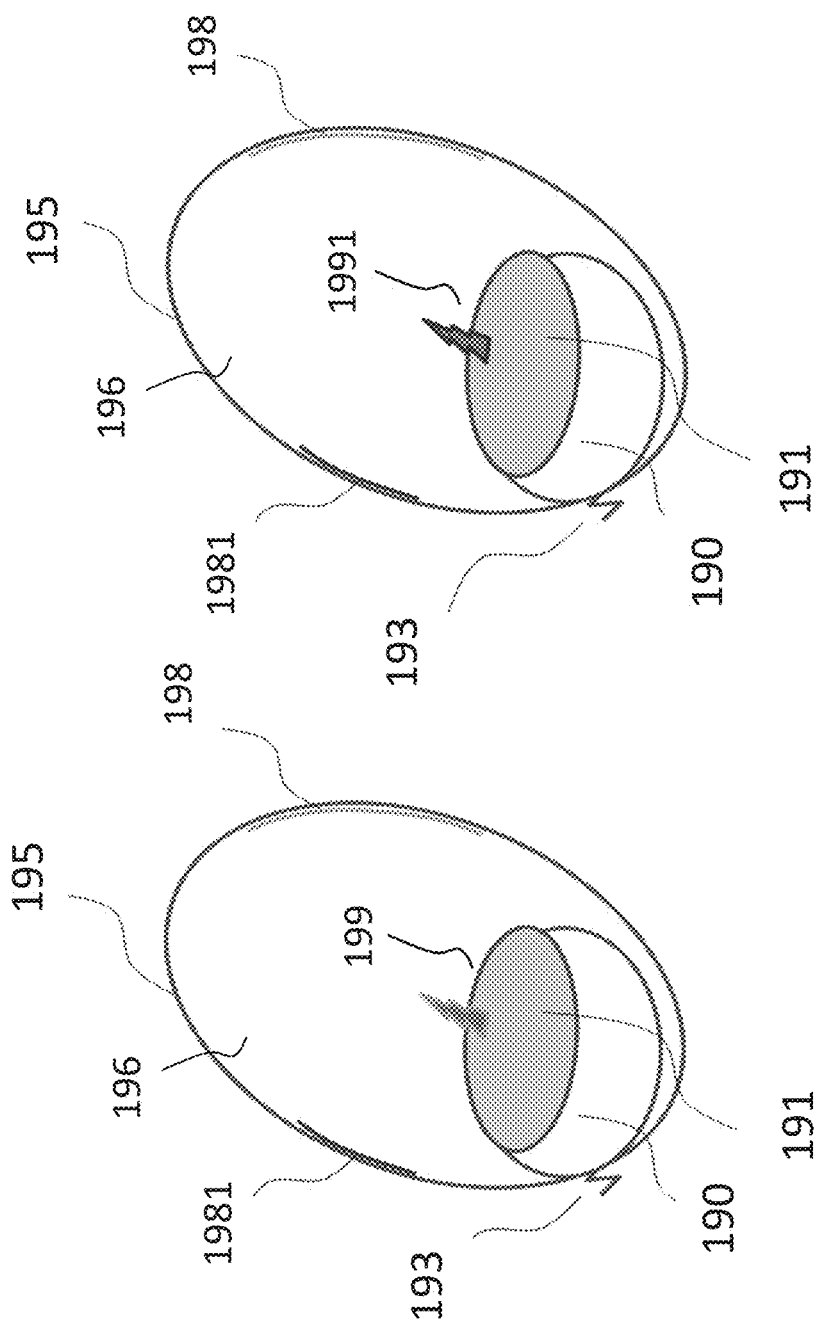
FIGS. 19A and 19B are examples with locally pretreated areas for stimulation by means of electromagnetic radiation.

FIGS. 19A and 19B show an example with locally pretreated areas 198 and 1981 which, however, are sensitive to different frequencies of the electromagnetic radiation. The selective effect of the therapy is achieved by an actuator 191 outputting electromagnetic radiation once at one frequency 199, as shown in FIG. 19A, and another time at another frequency 1991, as shown in FIG. 19B. Although an effective range 196 of the radiation covers all the tissue 195, the radiation only acts on the tissue in the regions 198 and 1981. The implant 190 is fastened to the organ tissue by means of a fixation device 193 and has an electromagnetic radiator 191.

Figure 20:
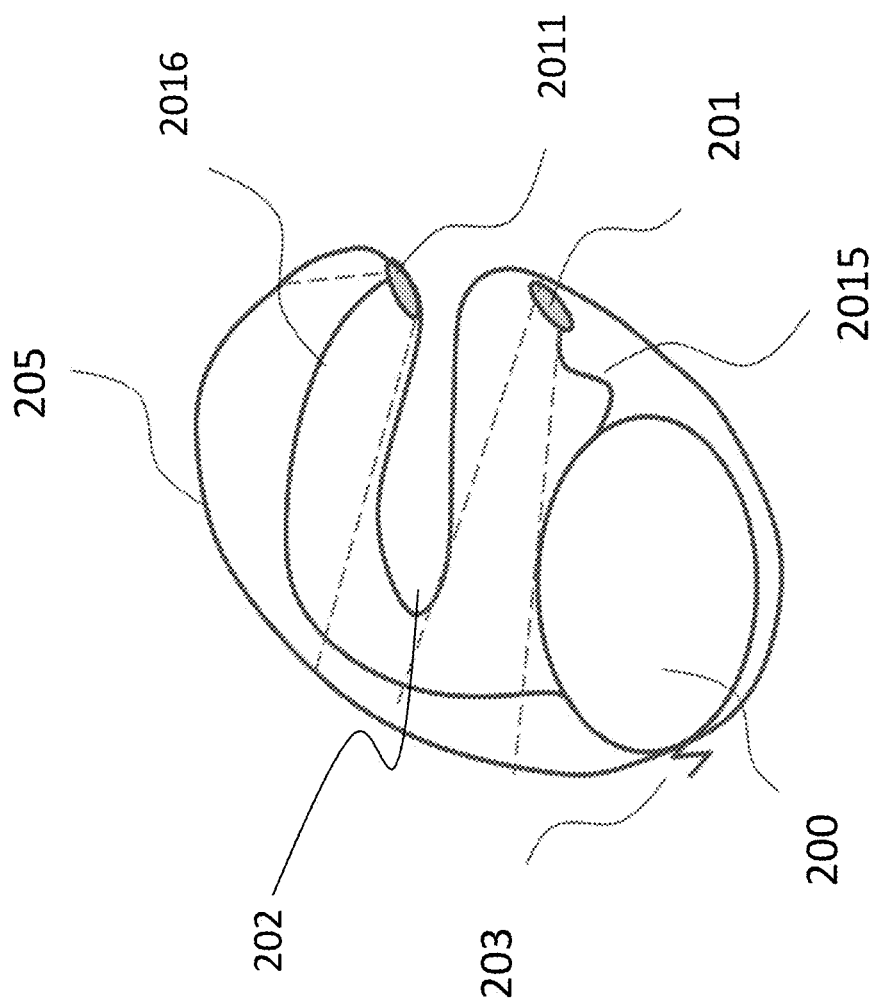
FIG. 20 schematic representation of selective therapy by placing the actuators to use the anatomical qualities of the tissue for shading, according to exemplary embodiments of this invention.

FIG. 20 shows an example of performing selective therapy by placing the actuators to make use of anatomical qualities of the tissue for shading. FIG. 20 shows how selective therapy is achieved by placing the actuators 201 and 2011 (connected with the stimulator 200 by leads 2015 and 2016) to make use of anatomical shapes 202 of the tissue 205 for shading. The implant 200 is fastened to the organ tissue by means of a fixation device 203.

Figure 21:
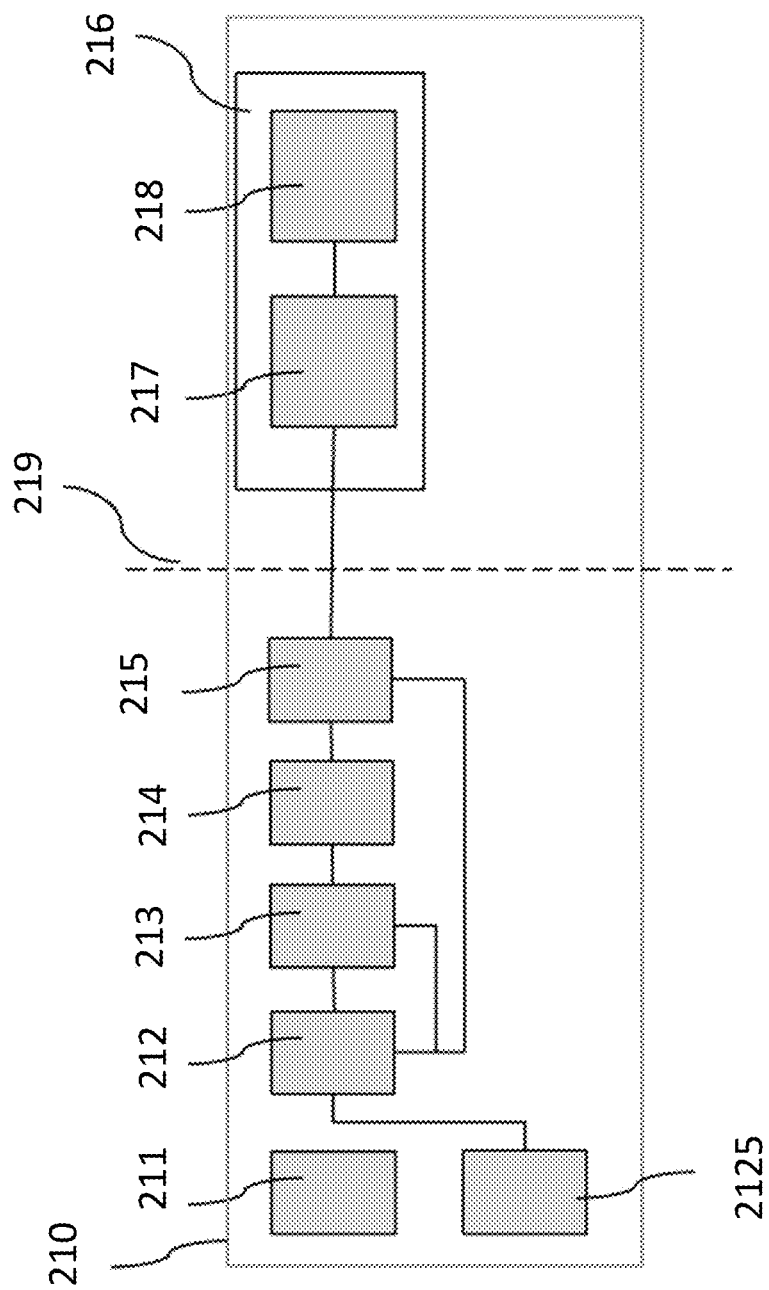
FIG. 21 block diagram of one embodiment of an inventive stimulator.

FIG. 21 shows the block diagram of the stimulator described in the claims that can output optical therapy. The stimulator 210 comprises an energy source 211, at least one energy storage 214, a charging device 213 for the energy storage 214, and a device for release of the energy 215. Also shown is an actuator 216 that has a light source 218 and a current limiter 217 (e.g., a resistor or a diode). The stimulator 210 has a controller 212. The stimulator 210 comprises a detection unit 2125. Actuator 216 can be implemented in the form of a unit that is separable from rest of the inventive device and can have an interface 219 for making contact.

Figure 22:
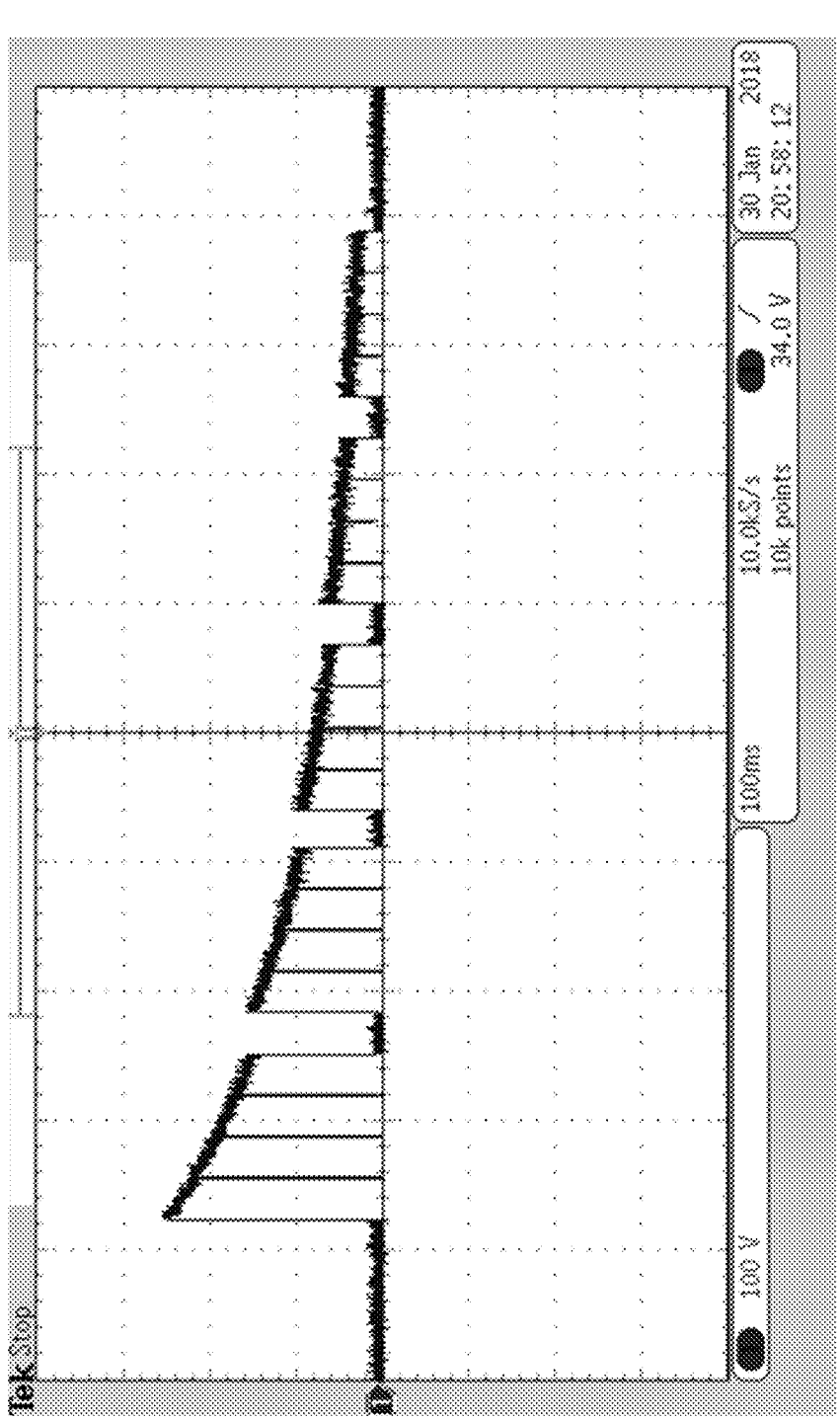
FIG. 22 is a graphical representation of the pulse discharge of an ICD, this pulse discharge controlling an inventive stimulator, which has the capability of performing therapy by means of electromagnetic radiation, so that the inventive stimulator delivers a pulsed therapy.

FIG. 22 shows the pulse discharge of an ICD, this pulse discharge controlling an inventive optical therapy actuator to output a pulsed therapy.

In one embodiment of the invention, already known electrical stimulation devices (e.g., cardiac pacemakers, neurostimulators) can be supplemented with an actuator for emitting electromagnetic radiation, to carry out stimulation by means of electromagnetic waves. Apart from the actuator, the stimulation device requires only slight modifications, or none at all.

FIG. 23 shows a table presenting exemplary combinations of stimulation and shock vectors between the right ventricle (RV), the housing of the stimulation device (CAN), and the right atrium (RA). For example, the second and third rows of the table represent a combination of two vectors: a first vector from housing CAN to right ventricle RV for the stimulation by an inventive actuator, and a second shock vector between housing CAN and the right atrium RA. In a commercially available ICD, these electrical poles can be implemented by a right ventricular shock coil, the ICD housing, and a supraventricular shock coil. In each case, a vector leads from a first pole marked by the cross to a second pole. The stimulation can be carried out by electromagnetic radiation through an inventive actuator, or by known electrical stimulation, or by a combination of the two.

Figure 24:
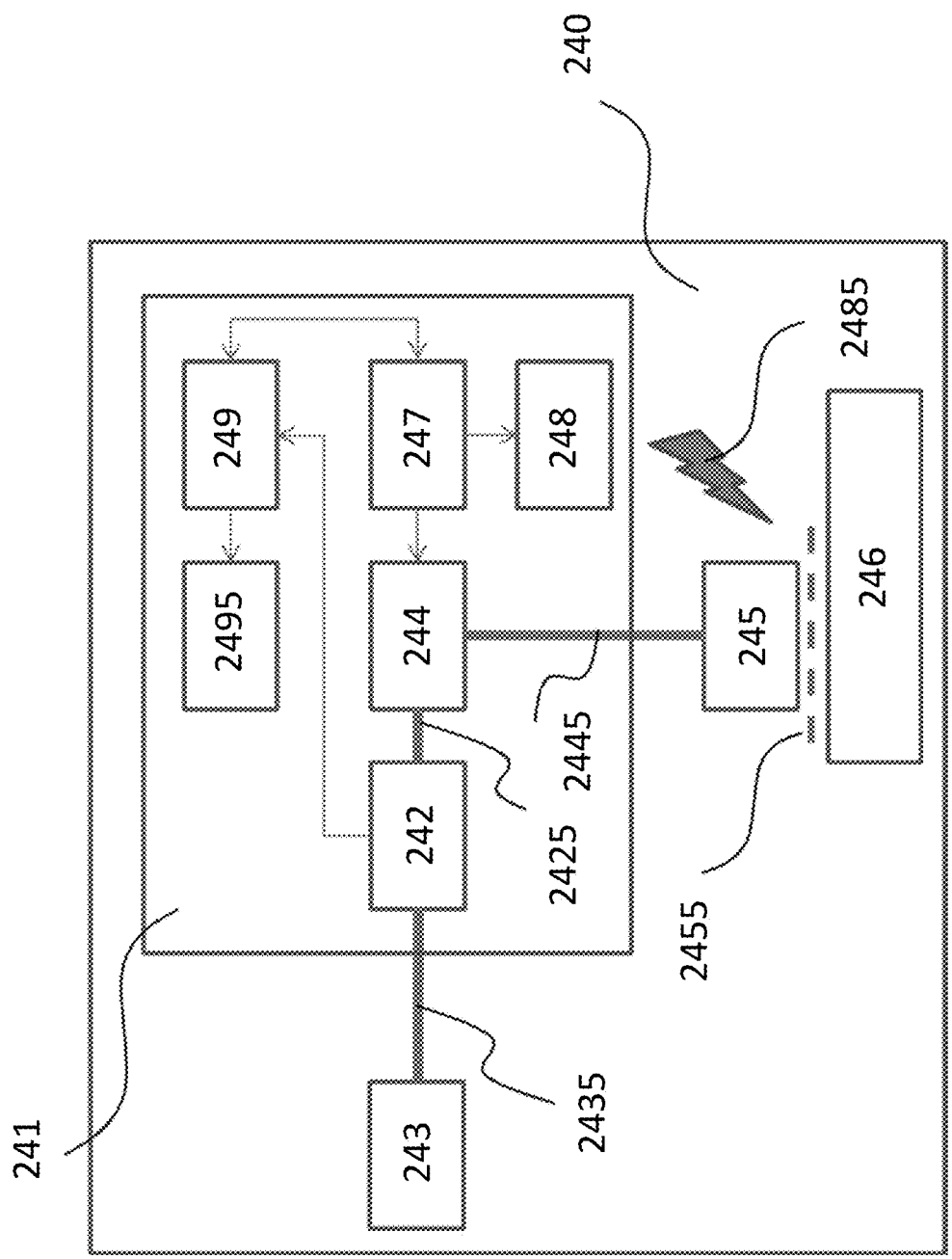
FIG. 24 is a block diagram of one embodiment of the inventive device in which the device comprises application means to deliver a substance to the tissue.

FIG. 24 is a block diagram of one embodiment of the inventive device comprising application means to deliver a substance to the tissue. The device 241 is implanted in the body 240. It has a reservoir 242 for the therapeutic substance and supply lines 2435, 2425, and 2445. The reservoir is filled through a port 243. Under the control of the controller 247, the pump pumps the substance to the device/tissue interface or application means 245, which treat the organ 246 with this substance through an optional mask 2455. A control unit 249 detects, among other things, the reservoir level and reports it externally through the telemetry unit 2495. To test the effectiveness, the therapy unit 248 outputs, under control of the controller 247, a test signal 2485. The reaction is detected by a detection unit (not shown) and reported to the control unit.

Figure 25:
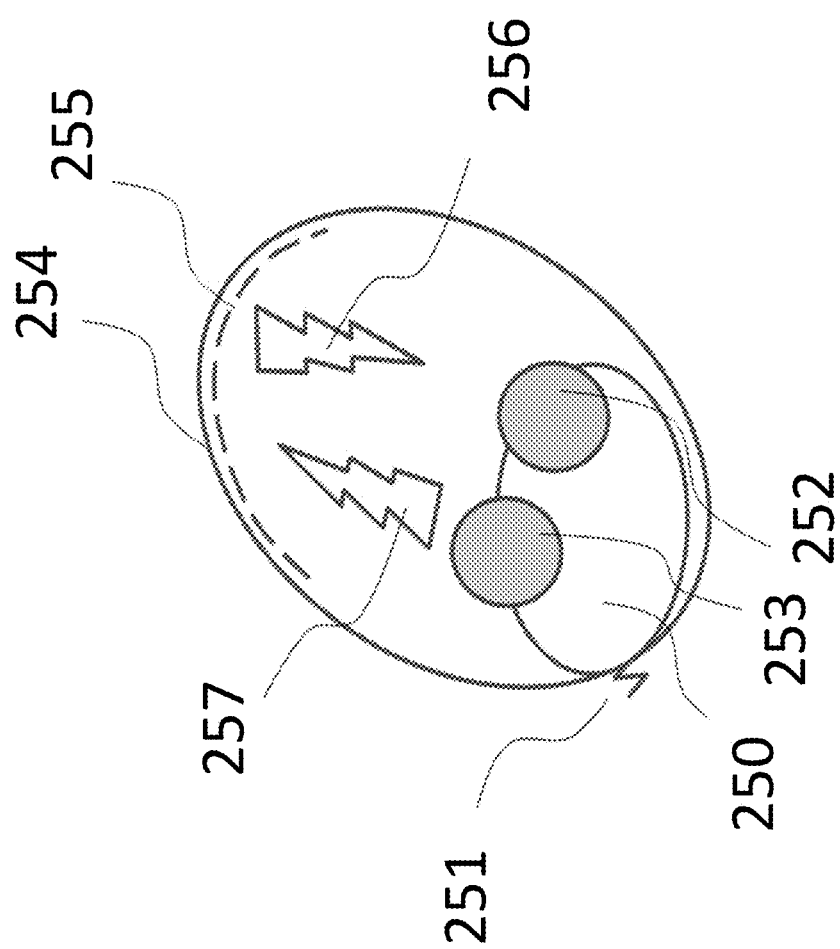
FIG. 25 schematic representation of one exemplary embodiment of the inventive implantable device, the device being fixed to the tissue by means of a fixation device.

FIG. 25 shows the inventive implantable device 250, which is fixed to the tissue 254 by means of a fixation device 251 and which has a sensor 252 to detect electromagnetic radiation 256 that exits as primary radiation from the excitable (optionally pretreated) cell structures 255 to be observed, if the latter form action potentials.

In an alternative implementation/application scenario, the implantable device 250 has an additional actuator 253 for the production of electromagnetic radiation 257. This electromagnetic radiation 257 is modulated by the excitable (optionally pretreated) cell structures 255 to be observed, depending on their action potentials, and returns to the sensor 252 in the form of secondary radiation 256.

Figure 26:
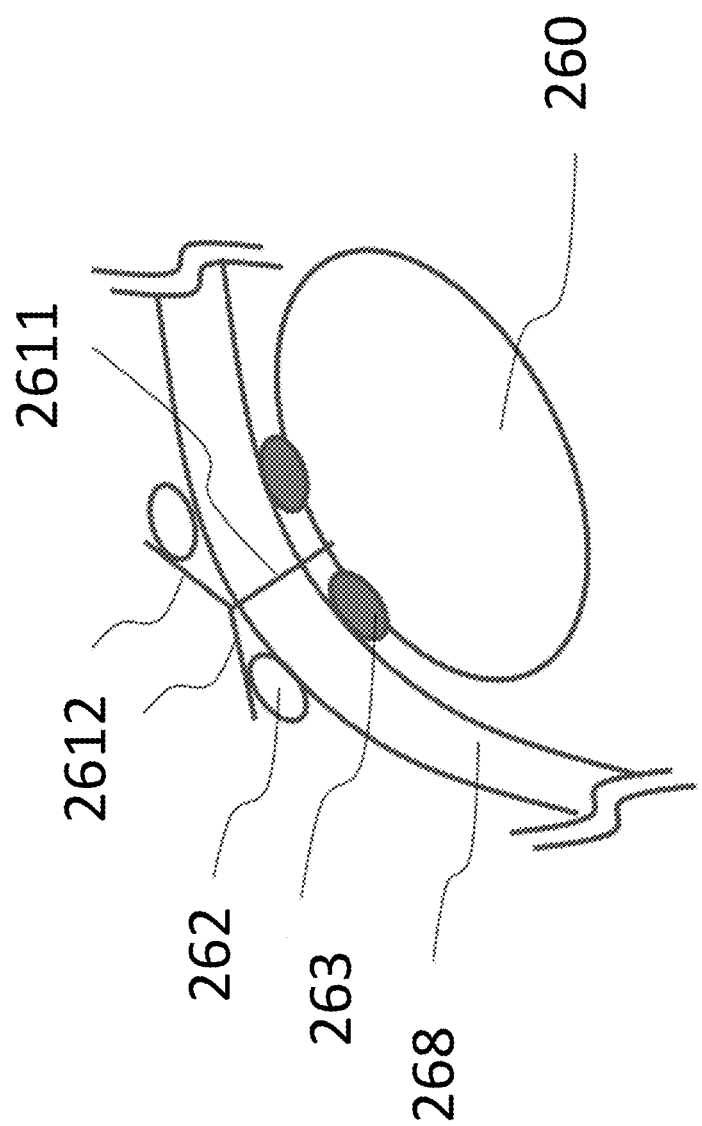
FIG. 26 schematic representation of one exemplary implementation of the inventive device. The device has actuators or sensors for electromagnetic radiation, which are incorporated into the fixation unit.
Figure 27:
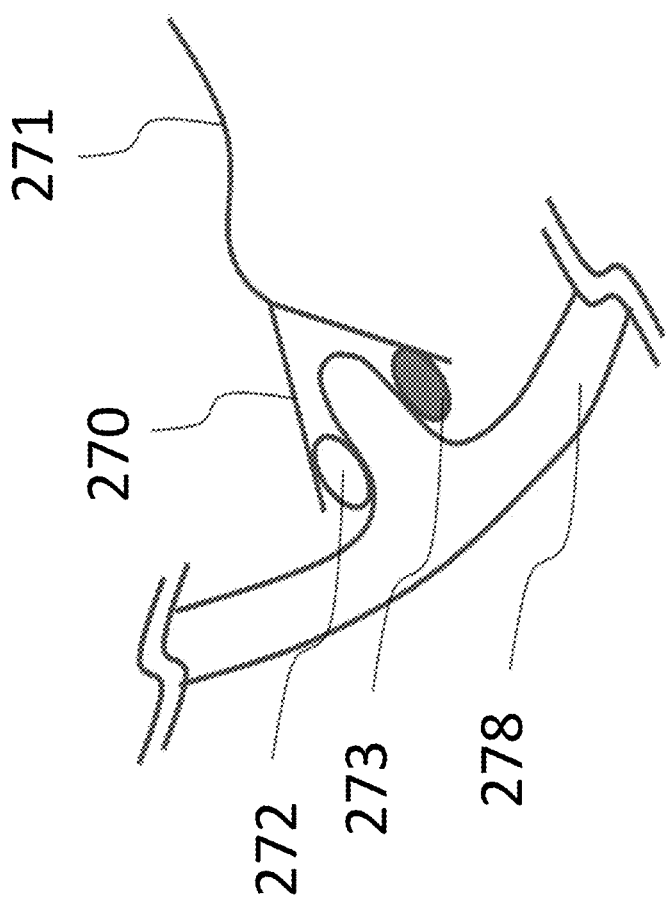
FIG. 27 schematic representation of another exemplary implementation of the inventive device. The device has actuators or sensors for electromagnetic radiation, which are incorporated into the fixation unit.

FIG. 26 discloses an implementation with actuators and sensors for electromagnetic radiation that are incorporated into the fixing unit. Here the fixing unit 261 consists of a shaft 2611 with folding, lockable arms 2612 that carry, e.g., the sensors 262. The actuators 263 are fixed opposite, e.g., on the housing 260. During implantation, the arms are aligned in the direction of the shaft, pushed through the organ wall 268, and then folded down and in locked in the position in which they lie opposite the actuators on the other side of the wall FIG. 27 discloses another implementation with actuators 273 and sensors 272 for electromagnetic radiation incorporated into the fixing unit. This involves the fixing unit 271 of the actuators 273 and sensors 272 being in the form of a pincer 270. A lead 271 leads to the device (not shown).

Figure 28:
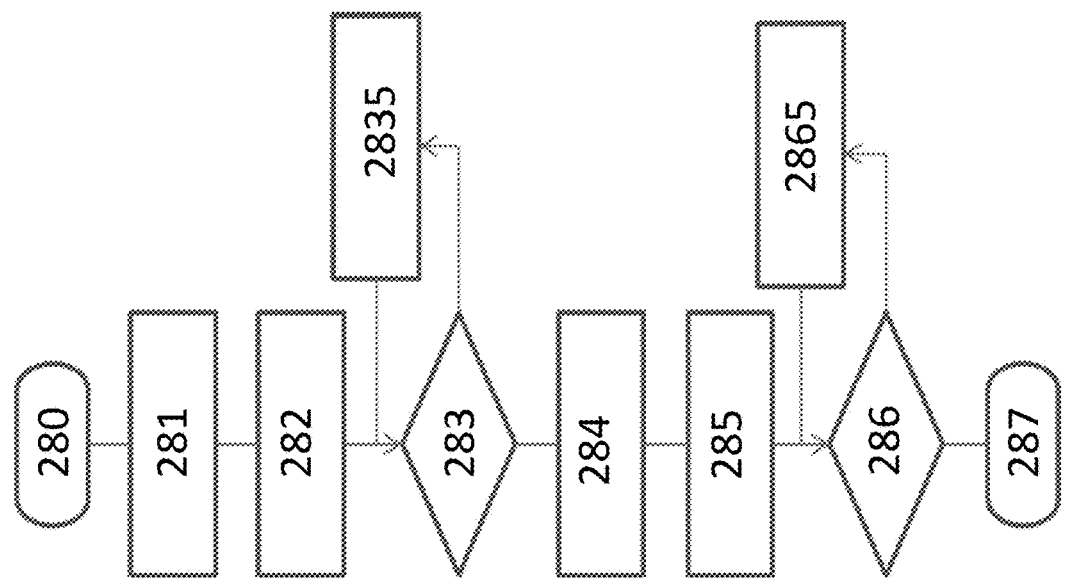
FIG. 28 shows an example of a preferred sequence of events in the signal processing of the inventive method.

FIG. 28 shows an example of the preferred sequence of events in an implantation according to the inventive method. The steps shown are:

280 starting the implantation
281 pretreating the target tissue
282 determining the suitable implantation site
283 positioning the device until the suitable implantation site is reached
2835 adjusting the position
284 fixing
285 setting parameters and starting the detection method (incl. processing and analysis)
286 testing
2865 adjusting the parameters
287 ending the implantation.

Figure 29:
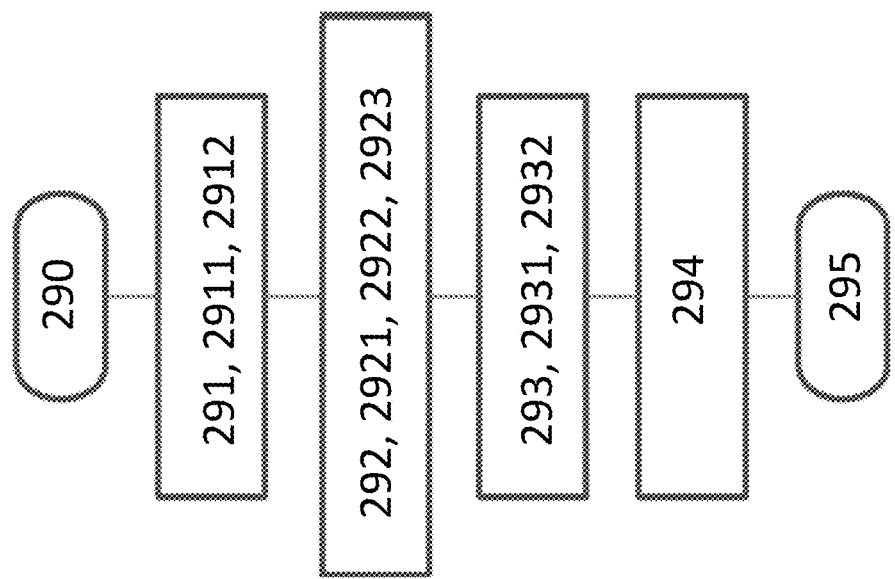
FIG. 29 shows an example of a sequence of events in the signal processing of the inventive method.

FIG. 29 shows an example of a preferred sequence of events in the signal processing of the inventive method. The steps shown are:

290 starting the detection (measurement)
291 amplifying,
2911 demodulating,
2912 analog filtering,
292 AD conversion;
2921 digital filtering;
2922 determining the signal strength;
2923 determining the threshold;
293 segmenting;
2931 event detection;
2932 determining periodicity;
294 classifying rhythms
295 ending the detection (measurement)

The invention entirely or partly eliminates the disadvantageous effects of galvanically coupled therapeutic electrical currents for the therapy of cardiac tissue, neuronal tissue, or muscle tissue.

This selective therapeutic approach opens new possibilities for multifocal therapy, without having to implant a separate probe for each stimulation site. The large-area multifocal therapy that it allows makes it possible to produce excitation patterns that represent natural spatiotemporal relationships much better than before.

The energy demand requirements of such implants can be substantially reduced. Furthermore, completely new designs of such implants are possible.

In the context of the invention, the following terms are used as synonyms for the inventive implantable device for detection of electromagnetic waves that are emitted from genetically manipulated tissue, and/or for stimulation of genetically manipulated tissue by means of electromagnetic waves: stimulator, stimulation device, device for stimulation, stimulation system (device is at least part of what is described as a stimulation system).

The following terms should be understood as follows:
"wave train" is understood to mean a continuous electromagnetic wave;
"electromagnetic radiation" and "electromagnetic wave" are synonyms;
ATP has the meaning "antitachycardia pacing";
IPG has the meaning "implantable pulse generator"; and
ICD has the meaning "implantable cardioverter-defibrillator".

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. A device, comprising:
an energy source;
an energy storage device;
an electronics unit;
an actuator connected to said energy storage device and configured to emit electromagnetic waves by discharging the energy storage device;
said electronics unit including a controller configured to adjust at least two impedances that are connected in series, said discharging taking place over said at least two series-connected impedances; and
wherein said at least two series-connected impedances are electrical switches.

2. The device according to claim 1 configured for implantation in a human or animal body.

3. The device according to claim 1, wherein said actuator is configured to at least one of detect or evoke action potentials in genetically manipulated tissue by emitting electromagnetic waves in a frequency range of $10^{13}$-$10^{20}$ Hz.

4. The device according to claim 1, wherein said energy storage device has at least one of a capacitor or a coil.

5. The device according to claim 1, wherein the discharge takes place in more than one phase.

6. The device according to claim 1, wherein said actuator has at least one of the following properties:
said actuator comprises at least one light source for emitting the electromagnetic waves;
said actuator comprises at least one current limiter;
said actuator is supplied by said energy storage device at a voltage between 1 V and 1,500 V;
said actuator is arranged separately from a housing of the device and has a plug-and-socket connector, which is compatible with a plug socket of an implantable device for electrical cardiac stimulation.

7. The device according to claim 6, wherein said actuator comprises said at least one light source for emitting the electromagnetic waves, said at least one light source including a series circuit of LEDs, or a parallel circuit of LEDs, or a combination of a series circuit and a parallel circuit of LEDs.

8. The device according to claim 6, wherein said actuator comprises said at least one light source for emitting the electromagnetic waves, said at least one light source including a laser light source.

9. The device according to claim 1, further comprising a telemetry unit with at least one of an external device or an external data center.

10. An implantable stimulation device, comprising a device according to claim 1 for a stimulation of cardiac tissue or nerve tissue structures.

11. The implantable stimulation device according to claim 10, further comprising at least one stimulation electrode.

12. The implantable stimulation device according to claim 10, configured to cause the stimulation of the cardiac tissue, the stimulation comprising at least one of the following:
stimulation by way of the actuator by electromagnetic waves; or
stimulation by electrical stimulation;
wherein the stimulation by electromagnetic waves and by electrical stimulation is effected individually, consecutively, or simultaneously; and
wherein the stimulation is effected in one area or in multiple areas of the tissue.

13. The implantable stimulation device according to claim 10, further comprising at least one of:
a plug contact that is compatible with an actuator according to claim 1; or
a plug contact that is compatible with an electrode for electrical stimulation; or
an actuator and an electrode.

* * * * *